(12) United States Patent
Sakai et al.

(10) Patent No.: US 8,642,630 B2
(45) Date of Patent: *Feb. 4, 2014

(54) ENDOGENEOUS REPAIR FACTOR PRODUCTION ACCELERATORS

(71) Applicant: Ono Pharmaceutical Co., Ltd., Osaka (JP)

(72) Inventors: Yoshiki Sakai, Osaka (JP); Akio Nishiura, Osaka (JP); Teppei Ogata, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/856,538

(22) Filed: Apr. 4, 2013

(65) Prior Publication Data

US 2013/0225643 A1    Aug. 29, 2013

Related U.S. Application Data

(62) Division of application No. 12/034,614, filed on Feb. 20, 2008, now Pat. No. 8,436,026, which is a division of application No. 10/530,685, filed as application No. PCT/JP03/12981 on Oct. 9, 2003, now Pat. No. 7,547,715.

(30) Foreign Application Priority Data

Oct. 10, 2002   (JP) ................. 2002-298079
Oct. 31, 2002   (JP) ................. 2002-318830
Apr. 22, 2003   (JP) ................. 2003-117604

(51) Int. Cl.
  *A61K 31/04*    (2006.01)
(52) U.S. Cl.
  USPC ......................... 514/353; 546/338
(58) Field of Classification Search
  USPC .......................... 514/353; 546/338
  See application file for complete search history.

(56) References Cited

U.S. PATENT DOCUMENTS 4,479,966 A   10/1984   Hayashi et al.
6,500,916 B1  12/2002   Hashida et al.

FOREIGN PATENT DOCUMENTS

| EP | 169725 | 3/1990 |
| EP | 0581187 | 2/1994 |
| EP | 860430 | 6/1999 |
| EP | 1121939 | 8/2001 |
| EP | 1175891 | 1/2002 |
| EP | 1563846 | 8/2005 |
| EP | 2087890 | 8/2009 |
| JP | 54130543 | 10/1979 |
| JP | 2000086517 | 3/2000 |
| JP | 2000239188 | 9/2000 |
| WO | 9909992 | 3/1999 |
| WO | 9926629 | 6/1999 |
| WO | 9943736 | 9/1999 |
| WO | 0003980 | 1/2000 |
| WO | 0116132 | 3/2001 |
| WO | 0172268 | 10/2001 |

OTHER PUBLICATIONS

Rosano, Cardio vasc Ent Technol, vol. 3(2), pp. 237-247, Jun. 2012 (myocardial infarction).*
Ma, PNAS, vol. 98(11), pp. 6470-6475, May 2001.*
Alber, HEart, vol. 91, pp. 365-366, 2005.*
Arakawa, heart, vol. 89, 207-208, 2003.*
Kwon, Clin & Mol HEpatology, vol. 18, pp. 287-294, 2012.*
Zhao, Circulation, vol. 105, pp. 1110-1115, 2002.*
Suzuki, Int Heart J, 53(1):64-67, 2012.*
Hirata, Eur J PHarmacol, 674(2 3):352-358, 2012.*
Hlrata, Biomed & aging Pathology, 1:90-96, 2011.*
Hirata, Blomed, Pharmacother, 3(10):731-736,2009.*
Iwata, Life Sci, 85(5-6): 255-261, 2009.*
Nakamura, CLin Sci (london), 112(12):607-616, 2007.*
Amano et al., "Enhancement by hepatocyte growth factor of bone and cartilage formation during embryonic mouse mandibular development in vitro", Archives of Oral Biology, 44:935-946 (1999).
Aoki et al., "HGF as a key molecule in cardiovascular diseases", Nippon Rinsho, 59(12): 2460-2469 (2001).
Aoki et al., "The latest review of therapeutic angiogenesis using angiogenic growth factors to peripheral arterial diseases", Nippon Rinsho, 60(9): 1845-1854 (2002).
Aoki et al., "Therapeutic Angiogenesis Induced by Hepatocyte Growth Factor: Potential Gene Therapy for Ischemic diseases", Journal of Atherosclerosis and Thrombosis, 7(2):71-76 (2000).
Barnes, "Novel Approaches and Targets for Treatment of Chronic Obstructive Pulmonary Disease", Am. J. Respir. Crit. Care Med., 160:S72-S79 (1999).
Booth et al., "Vascular endothelial growth factor in human periodontal disease", J. Periodont. Res., 33:491-499 (1998).
Cooper et al., "Increased Renal Expression of Vascular Endothelial Growth Factor (VEGF) and Its Receptor VEGFR-2 in Experimental Diabetes", Diabetes, 48:2229-2239 (1999).
European Office Action issued in European Patent Application No. 11010286.0, dated Feb. 19, 2013.
European Search Report issued in European Patent Application No. 11010286.0, dated May 22, 2012.
Feuerherm et al., "Elevated levels of osteoprotegerin (OPG) and hepatocyte growth factor (HGF) in rheumatoid arthritis", Scand. J. Rheumatol., 30:229-234 (2001).
Fuller et al., "The Effect of Hepatocyte Growth Factor on the Behaviour of Osteoclasts", Biochemical and Biophysical Research Communications, 212(2):334-340 (1995).

(Continued)

*Primary Examiner* — D M Seaman
(74) *Attorney, Agent, or Firm* — Sughrue Mion, PLLC

(57) ABSTRACT

It relates to an endogenous repair factor production accelerator which comprises one or at least two selected from prostaglandin (PG) I2 agonist, EP2 agonist and EP4 agonist. Since prostaglandin (PG) I2 agonist, EP2 agonist or EP4 agonist has various endogenous repair factor production accelerating action, angiogenesis acceleration action and stem cell differentiation induction action, it is useful as preventive and/or therapeutic agents for ischemic organ diseases (e.g., arteriosclerosis obliterans, Buerger disease, Raynaud disease, myocardial infarction, angina pectoris, diabetic neuropathy, spinal canal stenosis, cerebrovascular accidents, cerebral infarction, pulmonary hypertension, bone fracture, Alzheimer disease, etc.) and various cell and organ diseases.

16 Claims, 3 Drawing Sheets

(56) References Cited

OTHER PUBLICATIONS

Goto et al., "Hepatocyte Growth Factor in Glycerol-Induced Acute Renal Failure", Nephron, 77:440-444 (1997).
Griga et al., "Increased Serum Levels of Vascular Endothelial Growth Factor in Patients with Inflammatory Bowel Disease", Scand. J. Gastroenterol., 33: 504-508 (1998).
Hayashi et al., "Modulation of Anti-Glomerular Basement Membrane Nephritis in Rats by ONO-1301, a Non-Prostanoid Protaglandin $I_2$ Mimetic Compound with Inhibitory Activity against Thromboxane $A_2$ Synthase", Jpn. J. Pharmacol., 73:73-82 (1997).
Hayashi et al., "A prostacyclin agonist with thromboxane inhibitory activity for airway allergic inflammation in mice", Clinical Experimental Allergy, 40:317-326 (2009).
Hayashi et al., "Reduction of Ischemic Damage by Application of Vascular Endothelial Growth Factor in Rat Brain After Transient Ischemia", Journal of Cerebral Blood Flow and Metabolism, 18:887-895 (1998).
Hayek et al., "Growth Factor/Matrix-Induced Proliferation of Human Adult β-Cells", Diabetes, 44:1458-1460 (1995).
Hirata et al., "Synthetic prostacycline agonist, ONO-1301, ameliorates left ventricular dysfunction and cardiac fibrosis in cardiomyopathic hamsters", Biomedicine & Pharmacotherapy, 63:781-786 (2009).
Hoshino et al., "Gene expression of vascular endothelial growth factor and its receptors and angiogenesis in bronchial asthma", J. Allergy Clin. Immunol, 107:1034-1038 (2001).
Hu et al., "Hepatocyte Growth Factor is Increased in the Aqueous Humor of Glaucomatous Eyes", Journal of Glaucoma, 10:152-157 (2001).
Imai et al., "Hepatocyte Growth Factor Contributes to Facture Repair by Upregulating the Expression of BMP Receptors", Journal of Bone and Mineral Research, 20:1723-1730 (2005).
International Search Report issue in PCT/JP203/12981, dated Dec. 16, 2003.
Kalaria et al., "Vascular endothelial growth factor in Alzheimer's disease and experimental cerebral ischemia", Molecular Brain Research, 62:101-105 (1998).
Kasahara et al., "Endothelial Cell Death and Decreased Expression of Vascular Endothelial Growth Factor and Vascular Endothelial Growth Factor Receptor 2 in Emphysema", Am. J. Respir. Crit. Care Med., 163:737-744 (2001).
Kataoka et al., "A Long-Acting Prostacyclin Agonist with Thromboxane Inhibitory Activity for Pulmonary Hypertension", Am. J. Respir. Crit. Care Med., 172:1575-1580 (2005).
Kawaida et al., "Hepatocyte growth factor prevents acute renal failure and accelerates renal regeneration in mice", Proc. Natl. Acad. Sci., USA, 91:4357-4361 (1994).
Koike et al., "Prevention of onset of Parkinson's disease by in vivo gene transfer of human hepatocyte growth factor in rodent model: a model of gene therapy for Parkinson's disease", Gene Therapy, 13:1639-1644 (2006).
Kosai et al., "Hepatocyte Growth Factor Prevents Endotoxin-Induced Lethal Hepatic Failure in Mice", Hepatology, 30:151-159 (1999).
Laitinen et al., "Catheter-Mediated Vascular Endothelial Growth Factor Gene Transfer to Human Coronary arteries after Angioplasty", Human Gene Therapy, 11:263-270 (2000).
Miki et al., "Clinical significance of serum hepatocyte growth factor in orthotopic liver transplantation", Surgery, 119(5):505-510 (1996).
Mizuno et al., "Hepatocyte Growth Factor Prevents Renal Fibrosis and Dysfunction in a Mouse Model of Chronic Renal Disease", J. Clinc. Invest., 101:1827-1834 (1998).
Morishita et al., "Safety Evaluation of Clinical Gene Therapy Using Hepatocyte Growth Factor to Treat Peripheral Arterial Disease", Hypertension, 44(2): 203-209 (2004).
Murakami et al., "Prostacyclin agonist with thromboxane synthase inhibitory activity (ONO-1301) attenuates bleomycin-induced pulmonary fibrosis in mice", Am. J. Physiol. Lung Cell Mol. Physiol., 290: L59-L65 (2006).

Nagaraja et al., "Hepatocyte Growth Factor Levels in Gingival Crevicular Fluid in Health, Disease, and After Treatment", J. Periodontol., 78(4): 742-747 (2007).
Nasu et al., "Prostacyclin Analog ONO-1301 Ameliorates Tubulointerstitial Alterations through Induction of HGF", J. Am. Soc. Nephrol, 21: 267A (2010).
Nayeri et al., "Hepatocyte growth factor may accelerate healing in chronic leg ulcers: a pilot study", Journal of Dermatological Treatment, 13: 81-86 (2002).
Notification of Reasons for Refusal issued in Japanese Patent Application No. 2010-036052, dated Feb. 26, 2013.
Office Action issued in European Patent Application No. 03 754 060.6, dated Jul. 30, 2010.
Office Communication for Japanese Patent Application No. 2010-036052, dated Jul. 3, 2012.
Ohmichi et al., "Hepatocyte growth factor (HGF) acts as a mesenchyme-derived morphogenic factor during fetal lung development", Development, 125:1315-1324 (1998).
Okano et al., "Protective Action of Hepatocyte Growth Factor for Acute Liver Injury Caused by D-Galactosamine in Transgenic Mice", Hepatology, 26:1241-1249 (1997).
Ono. et al., "In vivo Gene Transfection with Hepatocyte Growth Factor via the Pulmonary Artery Induces Angiogenesis in the Rat Lung", Circulation, 106(Suppl. 1):I-264 to I-269 (2002).
Pfander et al., "Hepatocyte growth factor in human osteoarthritic cartilage", Osteoarthritis and Cartilage, 7:548-559 (1999).
Sakamaki et al., "Hepatocyte Growth Factor Stimulates Proliferation of Respiratory Epithelial Cells during Postpneumonectomy Compensatory Long Growth in Mice", Am. J. Respir. Cell Mol. Biol., 26:525-533 (2002).
Saki et al., "Prostaglandin E2 Regulates the Expression of Basic Fibroblast Growth Factor Messenger RNA in Normal Human Fibroblasts," Kobe J. Med. Sci., 47(35/45): 35-44 (2001).
Seno et al., "Cycloocygenase 2-and Prostaglandin $E_2$ Receptor $EP_2$-dependent Angiogenesis in Apc$^{716}$ Mouse Intestinal Polyps," Cancer Research, 62 506-511 (2002).
Shimamura et al., "Novel Therapeutic Strategy to Treat Brain Ischemia: Overexpression of Hepatocyte Growth Factor Gene Reduced Ischemic Injury Without Cerebral Edema in Rat Model", Circulation, 109:424-431 (2004).
Sugimura et al., "Production of Hepatocyte Growth Factor is Increased in Chronic Renal Failure", Nephron, 75:7-12 (1997).
Szabo et al., "Gene expression and gene therapy in experimental duodenal ulceration", Journal of Physiology Paris, 95:325-335 (2001).
Tahara et al., "Hepatocyte growth factor leads to recovery from alcohol-induced fatty liver in rats", J. Clin. Invest., 103:313-320 (1999).
Taniguchi et al., "Expression and Role of Vascular Endothelial Growth Factor in Liver Regeneration After Partial Hepatectomy in Rats", The Journal of Histochemistry & Cytochemistry, 49(1):121-129 (2001).
Taniyama et al., "Angiogenesis and Antifibrotic Action by Hepatocyte Growth Factor in Cardiomyopathy", Hypertension, 40:47-53 (2002).
Tsuboi et al., "Increased hepatocyte growth factor level in cerebrospinal fluid in Alzheimer's disease", Acta Neurol Scand., 107:81-86 (2003).
Tsuzuki et al., "Hepatocyte growth factor reduces the infarct volume after transient focal cerebral ischemia in rats", Neurological Research, 23: 417-424 (2001).
Ueda et al., "Hepatocyte Growth Factor Increases in Injured Organs and Functions as an Organotrophic Factor in Rats with Experimental Acute Pancreatitis", Pancreas, 20(1):84-93 (2000).
Ueki et al., "Hepatocyte growth factor gene therapy of liver cirrhosis in rats", Nature Medicine, 5(2):226-230 (1999).
Warzecha et al., "Hepatocyte growth factor attenuates pancreatic damage in caerulein-induced pancreatitis in rats", European Journal of Pharmacology, 430:113-121 (2001).
Yaekashiwa et al., "Simultaneous or Delayed Administration of Hepatocyte Growth Factor Equally Represses the Fibrotic Changes in Murine Lung Injury Induced by Bleomycin: A Morphologic Study", Am. J. Respir. Crit. Care Med., 156:1937-1944 (1997).

(56) References Cited

OTHER PUBLICATIONS

Yamasaki et al., "Intermittent Administration of ONO-1301, a Sustained-Release Prostacyclin Analog, Ameliorates Renal Alterations in Obese Type 2 Diabetes Mice", J. Am. Soc. Nephroi., 21: 689A (2010).

Yanagita et al., "Hepatocyte Growth Factor May Act as a Pulmotrophic Factor on Lung Regeneration after Acute Lung Injury", the Journal of Biological Chemistry, 268(28):21212-21217 (1993).

Zhang et al., "VEGF enhances angiogenesis and promotes blood-brain barrier leakage in the ischemic brain", J. Clin. Invest., 106: 829-838 (2000).

Ohmichi et al., "In vivo mitogenic action of HGF on lung epithelial cells: pulmotrophic role in lung regeneration", Am. J. Physiol., 270:L1031-L1039 (1996).

* cited by examiner

ENDOGENEOUS REPAIR FACTOR PRODUCTION ACCELERATORS

CROSS-REFERENCE TO RELATED APPLICATIONS

This application is a divisional of U.S. application Ser. No. 12/034,614, filed Feb. 20, 2008 (now allowed); which is a divisional of U.S. application Ser. No. 10/530,685 filed Apr. 8, 2005 (now U.S. Pat. No. 7,547,715); which is a National Stage application of PCT Application No. PCT/JP03/12981, filed Oct. 9, 2003; which claims priority of Japanese Application No. JP 2002-298079, filed Oct. 10, 2002; Japanese Application No. JP 2002-318830, filed Oct. 31, 2002; and Japanese Application No. JP 2003-117604, filed Apr. 22, 2003; the disclosure of each of which is incorporated herein by reference in their entirety.

TECHNICAL FIELD

The present invention relates to an endogenous repair factor production accelerator which comprises one or at least two selected from prostaglandin (hereinafter referred to as "PG") I2 agonist, EP2 agonist and EP4 agonist.

BACKGROUND ART

Regeneration medical treatment is drawing attention as the regeneration therapy at the time of disorders of tissues and cells such as blood vessel, liver, kidney, lung, pancreas, bone, skeletal muscle cell, myocardial cell, peripheral and central nerve cells and the like. The self repair system includes a system which is attained by the cell division of mature cells (simple duplication system) like the regeneration of many parenchymal organs such as liver and kidney and a system mediated by the proliferation and differentiation induction of stem cells (precursor cells) (stem cell system) like the regeneration of hematopoietic cells. Presently, it is said that these two systems are present in the regeneration of many tissues and organs. For example, it is said that these two systems are present also in the angiogenesis (regeneration), and there are an angiogenesis system based on the growth of neighboring vascular endothelial cells, vascular smooth muscle cells and the like, effected by the release of various endogenous repair factors (e.g., vascular endothelial growth factor (VEGF), hepatocyte growth factor (HGF), various fibroblast growth factors (a/b FGF), transformation growth factor-β (TGF-β), platelet derived growth factor (PDGF), angiopoietin, hypoxia inducing factor (HIF), insulin-like growth factor (IGF), bone morphogenetic protein (BMP), connective tissue growth factor (CTGF), epidermal growth factor (EGF), etc., growth factors of their families, and the like) from (vascular) endothelial cells, (vascular) smooth muscle cells, fibroblasts, synovial cells, epithelial cells, platelets, monocytes, lymphocytes, macrophages and the like of the injured (neighboring) region, and a vasculogenesis system in which blood vessel is formed by the differentiation induction of vascular endothelial stem cells from bone marrow cells of a matured individual, effected by the release of various inflammatory cytokines (e.g., IL-1, IL-4, IL-8, TNFα, IFNα/γ, G-CSF, GM-CSF, NO (nitric monoxide), etc.), and various endogenous repair factors.

Regarding the presence of stem cells (precursor cells), they are present not only in blood vessels but also in many tissues such as hepatocyte, pancreatic (β) cell, myocardial cell, kidney, lung, bone, joint, nerve, fat, skin and the like, and are proliferated and differentiation-induced by various endogenous repair factors, various inflammatory cytokines and the like.

When production of these endogenous repair factors is accelerated, formation of collateral circulation passage is accelerated by the effect of angiogenesis on the ischemic region. Also, it is known that prevention and treatment (repairing regeneration) of various organ disorders are accelerated by the differentiation induction action from various tissue stem cells. For example, it is known that HGF has a cell growth acceleration action, a morphogenesis inducing action, a differentiation inducing action, a wandering acceleration action, anti-apoptosis action and the like (e.g., see *Biochem. Biophys. Res. Commun.*, 239, 639-644 (1997), etc.). It is known that these endogenous repair factor production accelerations are effective for the prevention and/or treatment of, for example, liver diseases (e.g., fluminant hepatitis, acute hepatitis, hepatic cirrhosis, fatty liver, liver transplantation, etc.), kidney diseases (e.g., acute renal insufficiency, chronic renal insufficiency, etc.), lung diseases (e.g., acute pneumonia, pulmonary fibrosis, pulmonary hypertension, chronic obstructive pulmonary disease (COPD), asthma, etc.), pancreas diseases (e.g., diabetes mellitus, chronic pancreatitis, etc.), bone diseases (e.g., osteoarthritis, articular rheumatism, osteoporosis, bone fracture, periosteum injury, etc.), digestive organ diseases (e.g., gastric ulcer, duodenal ulcer, ulcerative colitis, Crohn disease, etc.), nerve degeneration diseases (e.g., stroke, Parkinson disease, Alzheimer disease, spinal canal stenosis, cerebrovascular accidents, moyamoya disease, etc.), diabetic complications (e.g., nerve disorder, skin ulcer, nephropathy, retinal disease, etc.), vascular endothelial cell diseases (e.g., restenosis after PTCA (percutaneous transluminal coronary angioplasty), arteriosclerosis, etc.), heart diseases (e.g., supraventricular tachyarrhythmia, congestive heart failure, coronary artery disease, sudden cardiomyopathy, dilated cardiomyopathy, etc.), dental diseases (e.g., periodontal disease, tooth extraction wound, oral wound, periodontal tissue disease, etc.), decubitus, glaucoma, alopecia and the like.

The regeneration therapy mediated by endogenous repair factors is drawing attention as an angiogenesis (regeneration) therapy and a tissue generation therapy at the time of the diseases of organs and tissues such as liver, pancreas, kidney, heart, central/peripheral nerves, blood vessel, tooth, eye, periosteum, bone and the like. This is drawing attention particularly as a regeneration therapy of serious ischemic organ diseases having no therapeutic methods, and several methods are examined on arteriosclerosis obliterans (hereinafter referred to as "ASO"), Buerger disease, Raynaud disease, cardiovascular diseases (e.g., myocardial infarction, angina pectoris, etc.), diabetic neuropathy, spinal canal stenosis, ischemic brain disease (e.g., cerebrovascular accidents, cerebral infarction, etc.), pulmonary hypertension, bone fracture, or Alzheimer disease and the like.

For example, patients of obstructive peripheral blood vessel diseases typified by ASO and Buerger disease show intermittent claudication, pain during resting and ulcer and necrosis of the legs, and finally it becomes unavoidable to undergo amputation of the legs. However, at present, there is no therapeutic method effective for these serious ASO patients. Since intravenous injection of PGE 1 and a vasodilator or platelet agglutination inhibitor as an oral agent of cilostazol do not show their effects on serious ASO patients, an intravascular treatment (balloon dilation or Stent insertion) and revascularization cannot be carried out. Recently, a gene therapy in which a VEGF gene plasmid and an HGF gene plasmid are directly administered by intramuscular injection into skeletal muscles of ischemic regions of the legs of these patients (cf. *Circulation*, 97, 1114-1123 (1998) and *Gene Therapy*, 8, 181-189 (2001)) has been clinically applied, and its effect is drawing attention. In addition, slow release preparations of a growth factor protein (e.g., a gelatin inclusion sheet) have also been subjected to basal examinations (*Circulation*, 106, Supple 2, II 350 (2002)).

On the other hand, an angiogenesis therapy in which vascular endothelial stem cells separated from bone marrow or peripheral blood of a patient are directly administered into the ischemic region of a leg by intramuscular injection is drawing attention and is carried out at several university hospitals which is also drawing attention (cf. *THE LANCET*, 360, 427-435 (1002)).

Introduction of these genes and stem cells directly into ischemic regions using a vascular catheter equipped with a low invasion needle became possible also in myocardial infarction and angina pectoris, and is under clinical application as an angiogenesis therapy. For example, it has been reported that ischemia is improved for unstable angina by injecting a VEGF gene plasmid directly into heart muscle (*Circulation*, 98, 2800-2804 (1998)). Also, it was considered that PDGF is concerned in the angiogenesis after stroke, because its increase was observed in nerve cell of the phenanbla (the tissue is not dead by infarction but cannot perform its function) region of infarct focus of a cerebral infarction patient (*Stroke*, 28, 564-573 (1997)). Gene therapy and the like using a vector to the brain via cerebrospinal fluid from cerebellomedullary cistern have also been attempted on the ischemic cerebrovascular accidents. These treatments are a therapeutic angiogenesis (regeneration) therapy which prompts development of collateral circulation passage to the ischemic region and is a tissue regeneration therapy by the differentiation induction of tissue stem cells. However, clinical application of these gene therapy and cell therapy have many problems in terms of ethics, safety (immunity, infection, cancer, etc.), flexibility, economy and the like.

As a reopening therapy at the time of blood vessel obstruction in ASO, myocardial infarction, angina pectoris, arteriosclerosis and the like, PTCA (percutaneous transluminal coronary angiopathy) has been carried out with good results. However, it is known that restenosis is induced by the injury of vascular endothelial cells around the obstruction due to forced vasodilation by balloon dilation, Stent indwelling and the like. As a method for preventing restenosis, a platelet agglutination inhibitor or the like is administered, but this is still an unsatisfactory state. Recently, drugs such as antibiotics and carcinostatic agents (rapamycin, sirolimus, etc.) and a Stent coated with a radioisotope preparation such as β rays have been developed with good results on the prevention of restenosis (*N. Eng. J. Med.*, 346(23), 1769-1771 (2002)). However, these methods also have many problems from a long-term point of view. Accordingly, concern is directed toward a medicament which enhances platelet agglutination inhibitory action at topical injured regions of vascular endothelial cells and damage repairing action by endothelial cell growth.

On the other hand, prostaglandin (PG) is a natural physiologically active substance biosynthesized from PGH2 in a metabolic pathway in the living body, which is called arachidonic acid cascade. The biosynthesis enzymes from arachidonic acid to PGH2 are called cyclooxygenase (COX), and COX-1, COX-2 and COX-3 are known at present (*Proc. Natl. Acad. Sci.*, 99, 1371 (2002)). In addition, compounds which inhibit these enzymes are generally used as antipyretic, analgesic and anti-inflammatory agents and agents for preventing circulatory organ system diseases, as non-steroidal anti-inflammatory drug (NSAID). Particularly, COX-2 induced in inflammation regions is concerned in the biosynthesis of PGI2, PGE2 and the like. These biosynthesized PGs are concerned in the onset of pyrexia, pain and inflammation in the inflammation regions and healing thereof. That is, the PGs biosynthesized at the inflammation regions directly act as inflammation-causing agents, induce various inflammatory cytokines, evoke inflammation, and accelerate healing thereof.

On the other hand, it is known that patients who took NSAID for a prolonged period of time have significantly low mortality rate by large bowel cancer and lung cancer (*N. Eng. J. Med.*, 328, 1313-1316 (1993)). It is said that this action has a cancer cell growth inhibitory action, because angiogenesis for cancer tissue growth is inhibited through the biosynthesis inhibition of PGI2, PGE2 and the like by NSAID. That is, an anti-angiogenesis therapy which controls growth and metastasis of tumors by inhibiting angiogenesis is drawing attention as a new strategy of cancer treatment. Also, it is known that a COX-2-selective inhibitor does not induce gastric ulcer when it is administered, but prolongs healing of gastric ulcer. There is a report stating that its cause is inhibition of angiogenesis action for repairing of injured tissues (*Am. J. Med.*, 104, 43S-51S (1998)). In addition, selective COX-2 inhibitors control the angiogenesis accompanied by inflammation (*Jpn. J. Pharmacol.*, 75, 105-114 (1997)).

It is known that PGI2 has a markedly strong platelet agglutination inhibitory action, as well as actions such as platelet adhesion, vasodilation and gastric acid secretion inhibition. In addition, PGE2 administration accelerates accumulation of inflammatory cells including monocyte and production of inflammatory cytokine (e.g., IL-1 (interleukin-1), IL-8, IL-6, IFN-α (interferon-α), TNFα (tumor necrosis factor α), and NO (nitric monoxide), etc.), and acts as an inflammation-causing agent.

JP-A-6-87811 discloses in its specification that the oxime derivative represented by formula (I) which is described later or a non-toxic salt thereof, to be used in the present invention as a PGI2 agonist (IP agonist), is useful for the prevention and/or treatment of thrombosis, arteriosclerosis, ischemic heart disease, gastric ulcer, hypertension and the like, because it has platelet agglutination inhibition, platelet adhesion inhibition, vasodilation and gastric acid secretion inhibition actions, but it does not describe or suggest on the angiogenesis action by exerting vascular endothelial cell and vascular smooth muscle cell growth action based on the endogenous repair factor production acceleration action, and on the various cell and organ diseases (the above-described diseases to be prevented and treated (repair regeneration) by HGF) by differentiation induction of various stem cells caused by these endogenous repair factor production acceleration action and the like.

Also, it is reported in *Diabetologia.*, 40, 1053-1061 (1997) that a PGI2 derivative Beraprost ((±)-(1R,2R,3aS,8bS)-2,3,3a,8b-terahydro-2-hydroxy-1-[(E)-(3S,4RS)-3-hydroxy-4-methyl-1-octen-6-ynyl]-1H-cyclopenta[b]benzofuran-5-butanoic acid sodium salt) increases HGF production in vascular endothelial cells in vitro and shows endothelial cell growth action, but there are no descriptions on the angiogenesis accelerating action by the topical administration of persistent preparation of Beraprost and on its usefulness for the prevention and treatment of various organ diseases.

In addition, PGE2 is known as a metabolic product in the arachidonic acid cascade, and it is known that its actions have various functions such as cell protection action, uterine contraction action, pain producing action, digestive organ peristalsis acceleration action, stimulation action, gastric acid secretion inhibition action, blood pressure reducing action, diuretic action and the like.

From the studies in recent years, it has been revealed that subtypes having respectively different roles are present in the PGE2 receptor. The subtypes known at present are roughly divided into four, and are respectively called EP1, EP2, EP3 and EP4 (*J. Lipid Mediators Cell Signaling*, 12, 379-391 (1995)). By examining their share of roles and thereby finding a compound which does not bind to other subtype receptors, it became possible to obtain a medicament having less side effects.

For example, JP-A-11-193268 discloses in its specification that a compound represented by formula (I-a), a non-toxic salt thereof, or a prodrug or cyclodextrin clathrate thereof, which is used in the present invention as an EP2 agonist, is useful in preventing and/or treating immune diseases (e.g., autoimmune disease, organ transplantation, etc.), asthma, osteogenesis abnormality, nerve cell death, hepatopathy, premature delivery, abortion, retinal nerve diseases such as glaucoma, and the like, but it does not describe or suggest on the endogenous repair factor releasing action, stem cell differentiation induction action and angiogenesis acceleration action.

For example, WO00/03980 discloses in its specification that a compound represented by formula (I-b), a non-toxic salt thereof, or a cyclodextrin clathrate thereof, which is used in the present invention as an EP4 agonist, is useful in preventing and/or treating diseases including immune diseases (amyotrophic lateral sclerosis (ALS), multiple sclerosis, Sjoegren syndrome, rheumatoid arthritis, autoimmune diseases such as systemic lupus erythematosus, rejection after organ transplantation, etc.), asthma, osteogenesis abnormality, nerve cell death, lung disease, hepatopathy, acute hepatitis, glomerulonephritis, renal insufficiency, hypertension, myocardial ischemia, systemic inflammatory reaction syndrome, burn pain, sepsis, hemophagocytosis syndrome, macrophage activation syndrome, Still disease, Kawasaki disease, burn injury, systemic granuloma, neoplastic colitis, Crohn disease, hypercytokinemia at the time of dialysis, multiple organ failure, shock, sleep abnormality, platelet agglutination and the like, but it does not describe or suggest on the endogenous repair factor releasing action, stem cell differentiation induction action and angiogenesis acceleration action.

DISCLOSURE OF THE INVENTION

Great concern has been directed toward the development of an endogenous repair factor production accelerator, a stem cell differentiation inducer (precursor cell differentiation inducer) and an angiogenesis accelerator, which are useful as preventive and therapeutic agents of (ischemic) organ diseases and have less side effects.

With the aim of finding an endogenous repair factor production accelerator, a stem cell differentiation inducer and an angiogenesis accelerator, which are useful as preventive and therapeutic agents of (ischemic) organ diseases, the present inventors have conducted intensive studies and found as a result that a PGI2 agonist (e.g., a compound represented by formula (I) or a salt thereof), an EP2 agonist (e.g., a salt represented by formula (I-a), a prodrug thereof or a cyclodextrin clathrate thereof) or an EP4 agonist (e.g., a compound represented by formula (I-b), a salt thereof or a cyclodextrin clathrate thereof) can achieve the object, thereby accomplishing the present invention.

Also, the inventors have considered that when a PGI2 agonist, an EP2 agonist or an EP4 agonist could be topically administered to an ischemic region requiring angiogenesis or a injured region requiring tissue repair, it will become possible to produce an endogeneous repair factor, an inflammatory cytokine and the like in the periphery of the injured topical region, in addition to the vasodilation of the remaining blood vessels in the ischemic region and platelet agglutination inhibitory action, so that a medicament having less side effects in systemic administration could be created. In addition, it was considered that when it is possible to produce a pharmaceutical preparation for persistent release during a period until angiogenesis (regeneration) or tissue repair is effected in the ischemic region or periphery of the tissue injury topical region, a medicament having less side effects in systemic administration and with improved administration compliance of small administration frequency could be created.

For example, angiogenesis requires a period of generally from 1 week to 6 months, more preferably from 1 week to 8 weeks, and persistent release of the active ingredient is required in the ischemic region during the period. In addition, since PGI2 agonists, EP2 agonists and EP4 agonists show vasodilation action and platelet agglutination inhibitory action in addition to angiogenesis acceleration action and vascular stem cell differentiation induction action when production of various endogenous growth factors is accelerated, it was considered that they will show further strong preventive and/or therapeutic effect upon ischemic organ diseases when these actions are added.

Thus, the inventors have also found as a result of intensive studies that a persistent preparation of a PGI2 agonist, an EP2 agonist or an EP4 agonist can achieve the above-described object, thus accomplishing the present invention.

That is, the present invention relates to the followings:
(1) An endogenous repair factor production accelerator, which comprises one or at least two selected from a PGI2 agonist, an EP2 agonist and an EP4 agonist.
(2) The endogenous repair factor production accelerator according to the above (1), wherein the endogenous repair factor is a vascular endothelial growth factor, a hepatocyte growth factor, a fibroblast growth factor, a transformation growth factor-β, a platelet derived growth factor, a bone morphogenetic protein or an epidermal growth factor.
(3) The endogenous repair factor production accelerator according to the above (1), which is a stem cell differentiation inducer.
(4) The endogenous repair factor production accelerator according to the above (1), which is an angiogenesis accelerator.
(5) The endogenous repair factor production accelerator according to the above (1), which is a persistent preparation which further comprises a biodegradable polymer.
(6) The endogenous repair factor production accelerator according to the above (5), wherein the persistent preparation is a microsphere preparation, a microcapsule preparation or a nanosphere preparation.
(7) The endogenous repair factor production accelerator according to the above (1), which is an agent for preventing and/or treating organ diseases.
(8) The endogenous repair factor production accelerator according to the above (7), wherein the organ disease is an ischemic organ disease, a liver disease, a kidney disease, a lung disease, a pancreas disease, a bone disease, a digestive organ disease, a nerve degeneration disease, a diabetic complication, a vascular endothelial cell disease, a heart disease, a dental disease, decubitus, glaucoma or alopecia.
(9) The endogenous repair factor production accelerator according to the above (8), wherein the ischemic organ disease is arteriosclerosis obliterans, Buerger disease, Raynaud disease, myocardial infarction, angina pectoris, diabetic neuropathy, spinal canal stenosis, cerebrovascular accidents, cerebral infarction, pulmonary hypertension, bone fracture or Alzheimer disease.

(10) The endogenous repair factor production accelerator according to the above (1), wherein the PGI2 agonist is a compound represented by formula (I):

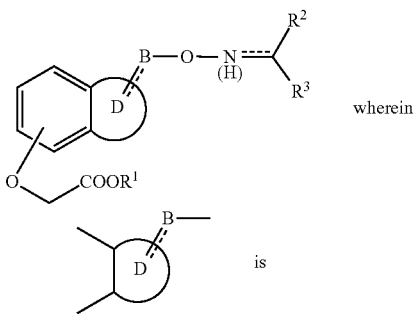

(I)

wherein

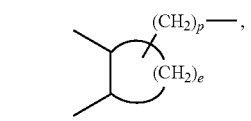

is

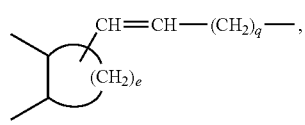

(i)

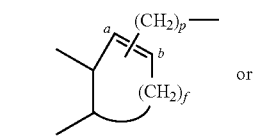

(ii)

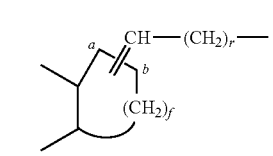

(iii)

or (iv)

wherein $R^1$ represents hydrogen or C1-4 alkyl;

$R^2$ represents (i) hydrogen, (ii) C1-8 alkyl, (iii) phenyl or C4-7 cycloalkyl, (iv) a 4- to 7-membered monocyclic ring containing one nitrogen atom, (v) C1-4 alkyl substituted with a benzene ring or C4-7 cycloalkyl, or (vi) C1-4 alkyl substituted with a 4- to 7-membered monocyclic ring containing one nitrogen atom;

$R^3$ represents (i) C1-8 alkyl, (ii) phenyl or C4-7 cycloalkyl, (iii) a 4- to 7-membered monocyclic ring containing one nitrogen atom, (iv) C1-4 alkyl substituted with a benzene ring or C4-7 cycloalkyl, or (v) C1-4 alkyl substituted with a 4- to 7-membered monocyclic ring containing one nitrogen atom;

e represents an integer of from 3 to 5;

f represents an integer of from 1 to 3;

p represents an integer of from 1 to 4;

r represents an integer of from 1 to 3;

q represents an integer of 1 or 2, and wherein, when

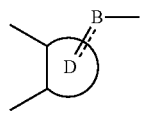

is the group represented by (iii) or (iv),
—$(CH_2)_p$— and =CH—$(CH_2)_s$— are bound to the position of a or b on the ring, and the rings in $R^2$ and $R^3$ may be substituted with 1 to 3 of C1-4 alkyl, C1-4 alkoxy, halogen, nitro or trihalomethyl, or a salt thereof.

(11) The endogenous repair factor production accelerator according to the above (10), wherein the PGI2 agonist is
(1) (E)-[5-[2-[1-phenyl-1-(3-pyridyl)methylideneaminoxy]ethyl]-7,8-dihydronaphthalen-1-yloxy]acetic acid, or
(2) (Z)-[5-[2-[1-phenyl-1-(3-pyridyl)methylideneaminoxy]ethyl]-7,8-dihydronaphthalen-1-yloxy]acetic acid.

(12) The endogenous repair factor production accelerator according to the above (1), wherein the PGI2 agonist is
(1) (±)-(1R,2R,3aS,8bS)-2,3,3a,8b-terahydro-2-hydroxy-1-[(E)-(3S,4RS)-3-hydroxy-4-methyl-1-octen-6-ynyl]-1H-cyclopenta[b]benzofuran-5-butanoic acid sodium salt,
(2) 5-{(3aR,4R,6aS)-5-hydroxy-4-[(1E,3S)-3-hydroxy-3-(cis-4-propylcyclohexyl)prop-1-enyl-3,3a,4,5,6,6a-hexahydrocyclopenta[b]pyrrol-2-yl}pentanoic acid methyl ester, or
(3) (5E)-5-[(3aS,4R,5R,6aS)-4-[(1E,3S)-3-cyclopentyl-3-hydroxyprop-1-enyl]-5-hydroxyhexahydropentalene-2 (1H)-ylidene]pentanoic acid.

(13) The endogenous repair factor production accelerator according to the above (1), wherein the EP2 agonist is a compound represented by formula (I-a):

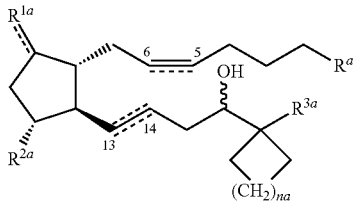

(I-a)

wherein $R^a$ represents carboxyl or hydroxymethyl;
$R^{1a}$ represents oxo, methylene or halogen;
$R^{2a}$ represents hydrogen, hydroxyl or C1-4 alkoxy;
$R^{3a}$ represents hydrogen, C1-8 alkyl, C2-8 alkenyl, C2-8 alkynyl, or C1-8 alkyl, C2-8 alkenyl or C2-8 alkynyl substituted with 1 to 3 of the following groups (1) to (5): (1) halogen, (2) C1-4 alkoxy, (3) C3-7 cycloalkyl, (4) phenyl, (5) phenyl substituted with 1 to 3 halogen, C1-4 alkyl, C1-4 alkoxy, nitro or trifluoromethyl;

na represents 0 or an integer of from 1 to 4;

--- represents a single bond or a double bond;

═══ represents a double bond or a triple bond; and

≡≡≡ represents a single bond, a double bond or a triple bond, and wherein (1) when the 5-6 position represents a triple bond, the 13-14 position does not represent a triple bond, and
(2) when the 13-14 position represents a double bond, the a double bond represents E form, Z form or EZ form, a salt thereof, a prodrug thereof or a cyclodextrin clathrate thereof.

(14) The endogenous repair factor production accelerator according to the above (13), wherein the EP2 agonist is (5Z, 9β,11α,13E)-17,17-propano-11,16-dihydroxy-9-chloro-20-norprost-5,13-dienoic acid.

(15) The endogenous repair factor production accelerator according to the above (1), wherein the EP4 agonist is a compound represented by formula (I-b):

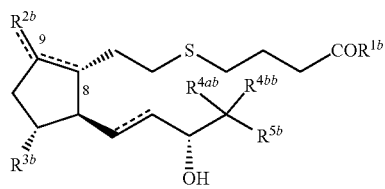

wherein $R^{1b}$ represents hydroxyl, C1-6 alkoxy or —$NR^{6b}R^{7b}$;
$R^{6b}$ and $R^{7b}$ each independently represents hydrogen or C1-4 alkyl;
$R^{2b}$ represents oxo, halogen or —O—$COR^{8b}$;
$R^{8b}$ represents C1-4 alkyl, phenyl or phenyl(C1-4 alkyl);
$R^{3b}$ represents hydrogen or hydroxyl;
$R^{4ab}$ and $R^{4bb}$ each independently represents hydrogen or C1-4 alkyl;
$R^{5b}$ represents phenyl substituted with a group of the following i) to iv):
i) 1 to 3 of
  C1-4 alkoxy-C1-4 alkyl,
  C2-4 alkenyloxy-C1-4 alkyl,
  C2-4 alkynyloxy-C1-4 alkyl,
  C3-7 cycloalkyloxy-C1-4 alkyl,
  C3-7 cycloalkyl(C1-4 alkoxy)-C1-4 alkyl,
  phenyloxy-C1-4 alkyl,
  phenyl-C1-4 alkoxy-C1-4 alkyl,
  C1-4 alkylthio-C1-4 alkyl,
  C2-4 alkenylthio-C1-4 alkyl,
  C2-4 alkynylthio-C1-4 alkyl,
  C3-7 cycloalkylthio-C1-4 alkyl,
  C3-7 cycloalkyl(C1-4 alkylthio)-C1-4 alkyl,
  phenylthio-C1-4 alkyl, or
  phenyl-C1-4 alkylthio-C1-4 alkyl,
ii) C1-4 alkoxy-C1-4 alkyl and C1-4 alkyl,
  C1-4 alkoxy-C1-4 alkyl and C1-4 alkoxy,
  C1-4 alkoxy-C1-4 alkyl and hydroxy,
  C1-4 alkoxy-C1-4 alkyl and halogen,
  C1-4 alkylthio-C1-4 alkyl and C1-4 alkyl,
  C1-4 alkylthio-C1-4 alkyl and C1-4 alkoxy,
  C1-4 alkylthio-C1-4 alkyl and hydroxy, or
  C1-4 alkylthio-C1-4 alkyl and halogen,
iii) haloalkyl or hydroxy-C1-4 alkyl, or
iv) C1-4 alkyl and hydroxy; and
  ═══ represents a single bond or a double bond, and
wherein, when $R^{2b}$ is —O—$COR^{8b}$, the 8-9 position represents a double bond,
a salt thereof or a cyclodextrin clathrate thereof.

(16) The endogenous repair factor production accelerator according to the above (15), wherein the EP4 agonist is
(1) (11α,13E,15α)-9-oxo-11,15-dihydroxy-16-(3-methoxymethylphenyl)-17,18,19,20-tetranor-5-thiaprost-13-enoic acid, or
(2) (11α,13E,15α)-9-oxo-11,15-dihydroxy-16-(3-methoxymethylphenyl)-17,18,19,20-tetranor-5-thiaprost-13-enoic acid methyl ester.

(17) A method for accelerating production of an endogenous repair factor in a mammal, which comprises administering to a mammal an effective amount of one or at least two selected from a PGI2 agonist, an EP2 agonist and an EP4 agonist.

(18) A method for preventing and/or treating organ diseases in a mammal, which comprises administering to a mammal an effective amount of one or at least two selected from a PGI2 agonist, an EP2 agonist and an EP4 agonist.

(19) Use of one or at least two selected from a PGI2 agonist, an EP2 agonist and an EP4 agonist for preparing an endogenous repair factor production accelerator.

(20) Use of one or at least two selected from a PGI2 agonist, an EP2 agonist and an EP4 agonist for preparing an agent for preventing and/or treating organ diseases.

(21) A pharmaceutical composition which comprises the endogenous repair factor production accelerator according to the above (1) in combination with one or at least two selected from an anti-thrombus agent, a circulation improving agent, a bronchial smooth muscle dilator, an anti-inflammatory drug, a local anesthetic, an analgesic, a bone cement, an joint lubricant, a PG derivative, an endogenous repair factor protein, an endogenous repair factor gene and a stem cell.

In the specification, examples of the C1-4 alkyl include straight chain or branched chain C1-4 alkyl such as methyl, ethyl, n-propyl, isopropyl, n-butyl, isobutyl, sec-butyl and tert-butyl, and the like.

In the specification, examples of the C1-6 alkyl include straight chain or branched chain C1-6 alkyl such as methyl, ethyl, n-propyl, isopropyl, n-butyl, isobutyl, sec-butyl, tert-butyl, pentyl and hexyl, and the like.

In the specification, examples of the C1-8 alkyl include straight chain or branched chain C1-8 alkyl such as methyl, ethyl, n-propyl, isopropyl, n-butyl, isobutyl, sec-butyl, tert-butyl, pentyl, hexyl, heptyl and octyl, and the like.

In the specification, examples of the C2-8 alkenyl include straight chain or branched chain C2-8 alkenyl such as ethenyl, propenyl, butenyl, pentenyl, hexenyl, heptenyl and octenyl, and the like.

In the specification, examples of the C2-8 alkynyl include straight chain or branched chain C2-8 alkynyl such as ethynyl, propynyl, butynyl, pentynyl, hexynyl, heptynyl and octynyl, and the like.

In the specification, examples of the C1-4 alkoxy include straight chain or branched chain C1-4 alkoxy such as methoxy, ethoxy, n-propoxy, isopropoxy, n-butoxy, isobutoxy, sec-butoxy and tert-butoxy, and the like.

In the specification, examples of the C1-6 alkoxy include straight chain or branched chain C1-6 alkoxy such as methoxy, ethoxy, n-propoxy, isopropoxy, n-butoxy, isobutoxy, sec-butoxy, tert-butoxy, pentyloxy and hexyloxy, and the like.

In the specification, examples of the C2-4 alkenyloxy include straight chain or branched chain C2-4 alkenyloxy such as ethenyloxy, propenyloxy and butenyloxy, and the like.

In the specification, examples of the C2-4 alkynyloxy include straight chain or branched chain C2-4 alkynyloxy such as ethynyloxy, propynyloxy and butynyloxy, and the like.

In the specification, examples of the C1-4 alkylthio include straight chain or branched chain C1-4 alkylthio such as methylthio, ethylthio, n-propylthio, isopropylthio, n-butylthio, isobutylthio, sec-butylthio and tert-butylthio, and the like.

In the specification, examples of the C2-4 alkenylthio include straight chain or branched chain C2-4 alkenylthio such as ethenylthio, propenylthio and butenylthio, and the like.

In the specification, examples of the C2-4 alkynylthio include straight chain or branched chain C2-4 alkynylthio such as ethynylthio, propynylthio and butynylthio, and the like.

In the specification, examples of the halogen include fluorine, chlorine, bromine and iodine atoms and the like.

In the specification, examples of the trihalomethyl include methyl tri-substituted with iodine atom, bromine atom, fluorine atom or chlorine atom.

In the specification, examples of the C4-7 cycloalkyl include cyclobutyl, cyclopentyl, cyclohexyl, cycloheptyl and the like.

In the specification, examples of the C3-7 cycloalkyl include cyclopropyl, cyclobutyl, cyclopentyl, cyclohexyl, cycloheptyl and the like.

In the specification, examples of the 4- to 7-membered monocyclic ring containing one nitrogen atom include azete, azole, pyridine and azepin rings or rings in which these rings are partially or entirely saturated.

In the specification, examples of the C3-7 cycloalkyloxy include cyclopropyloxy, cyclobutyloxy, cyclopentyloxy, cyclohexyloxy, cycloheptyloxy and the like.

In the specification, examples of the C3-7 cycloalkylthio include cyclopropylthio, cyclobutylthio, cyclopentylthio, cyclohexylthio, cycloheptylthio and the like.

In the specification, examples of the prodrug of the compound represented by formula (I-a) include (1) a compound in which $R^a$ is $COOR^{10a}$ ($R^{10a}$ represents C1-6 alkyl), (2) a compound in which $R^a$ is $CONR^{12a}R^{13a}$ ($R^{12a}$ and $R^{13a}$ each independently represents hydrogen or C1-6 alkyl), and (3) a compound in which $R^a$ is $COOR^{10a}$ ($R^{10a}$ has the same meaning as described above), $R^{1a}$ is $R^{11a}$—COO ($R^{11a}$ represents C1-4 alkyl, C1-4 alkoxy, phenyl, phenyl-C1-4 alkyl, $R^{14a}$—OOC—C1-4 alkyl or $R^{14a}$—OOC—C2-4 alkenyl ($R^{14a}$ represents hydrogen or C1-4 alkyl), and the 8-9 position is a double bond.

In the specification, examples of the endogenous repair factor include vascular endothelial growth factor (VEGF), hepatocyte growth factor (HGF), various fibroblast growth factors (a/b FGF), transformation growth factor-β (TGF-β), platelet derived growth factor (PDGF), angiopoietin, hypoxia inducing factor (HIF), insulin-like growth factor (IGF), bone morphogenetic protein (BMP), connective tissue growth factor (CTGF), epidermal growth factor (EGF) and the like, growth factors of their families and the like.

According to the description, for example, an IP agonist is also included in the PGI2 agonist.

According to the description, a prodrug is also included in the PGI2 agonist, EP2 agonist or EP4 agonist. The prodrug is a compound which is converted into its active form by through its reaction with an enzyme, gastric acid or the like in the living body. As the prodrug of the PGI2 agonist, EP2 agonist or EP4 agonist, for example when the PGI2 agonist, EP2 agonist or EP4 agonist has amino group, examples include compounds in which the amino group is acylated, alkylated or phosphorylated (e.g., compounds in which the amino group of the PGI2 agonist, EP2 agonist or EP4 agonist is eicosanoylated, alanylated, pentylaminocarbonylated, (5-methyl-2-oxo-1,3-dioxolan-4-yl)methoxycarbonylated, tetrahydrofuranylated, pyrrolidylmethylated, pivaloyloxymethylated, acetoxymethylated or tert-butylated); when the PGI2 agonist, EP2 agonist or EP4 agonist has hydroxyl group, examples include compounds in which the hydroxyl group is acylated, alkylated, phosphorylated or borated (e.g., compounds in which the hydroxyl group of the PGI2 agonist, EP2 agonist or EP4 agonist is acetylated, palmitoylated, propanoylated, pivaloylated, succinylated, fumarylated, alanylated or dimethylaminomethylcarbonylated); and when the PGI2 agonist, EP2 agonist or EP4 agonist has carboxyl, examples include compounds in which the carboxyl is esterificated or amidated (e.g., compounds in which the carboxyl of the PGI2 agonist, EP2 agonist or EP4 agonist is ethyl esterificated, phenyl esterificated, carboxymethyl esterificated, dimethylaminomethyl esterificated, pivaloyloxymethyl esterificated, ethoxycarbonyloxyethyl esterificated, phthalidyl esterificated, (5-methyl-2-oxo-1,3-dioxolan-4-yl) methyl esterificated, cyclohexyloxycarbonylethyl esterificated or methylamidated). These compounds can be produced by conventionally known methods. Also, prodrugs of the PGI2 agonist, EP2 agonist or EP4 agonist may be either hydrate or non-hydrate. In addition, prodrugs of the PGI2 agonist, EP2 agonist or EP4 agonist may be those which are changed into the compounds represented by formula (I) under physiological conditions, as described in *Iyakuhin-no Kaihatsu* (*Development of Pharmaceutical Preparations*), volume 7 "Bunshi Sekkei (Molecular Design)", pp. 163-198, edited in 1990 by Hirokawa Shoten.

Unless otherwise noted, all isomers are included in the present invention. For example, those of straight chain and branched chain are included in alkyl, alkenyl, alkynyl, alkoxy, alkylthio, alkylene, alkenylene and alkynylene. In addition, all of the isomers regarding a double bond, ring and condensed ring (E, Z, cis and trans isomers), isomers based on the presence of asymmetric carbon and the like (R and S isomers, α and β configurations, enantiomers and diastereomers), optically active substances having optical activity (D, L, d and l forms), polar forms by chromatographic separation (high polar form and low polar form), symmetrical compounds, rotational isomers and their mixtures having optional ratio and racemic mixtures are included in the present invention.

According to the present invention, unless otherwise noted and is evident to those skilled in the art, ⫽ means that it is bonded to the opposite side of the space (namely α configuration), ⫽ means that it is bonded to this side of the space (namely β configuration), ⫽ means that it is α configuration, β configuration or a mixture thereof, and ⫽ means the it is a mixture of α configuration and β configuration.

All of pharmacologically acceptable salts are included in the salts of the compounds represented by formula (I), formula (I-a) and formula (I-b). It is preferable that the pharmacologically acceptable salts do not have toxicity and are soluble in water. Examples of the suitable salt of the compound represented by formula (I) include salts of alkali metals (potassium, sodium, lithium, etc.), salts of alkaline earth metals (calcium, magnesium, etc.), ammonium salts (tetramethylammonium salt, tetrabutylammonium salt, etc.), salts of organic amines (triethylamine, methylamine, dimethylamine, cyclopentylamine, benzylamine, phenethylmine, piperidine, monoethanolamine, diethanolamine, tris(hydroxymethyl)methylamine, lysine, arginine, N-methyl-D-glucamine, etc.), and acid addition salts (inorganic acid salts (hydrochloride, hydrobromide, hydroiodide, sulfate, phosphate, nitrate, etc.), organic acid salts (acetate, trifluoroacetate, lactate, tartarate, oxalate, fumarate, maleate, benzoate, citrate, methanesulfonate, ethanesulfonate, benzenesulfonate, toluenesulfonate, isethionate, glucuronate, gluconate, etc.) and the like). Also included in the salts of the compounds of the present invention are solvates, or solvates of alkali (alkaline earth) metal salts, ammonium salts, organic amine salts and acid addition salts of the compounds of the present invention. It is preferable that the solvates are nontoxic and soluble in water. Examples of appropriate solvate include solvates of water, alcohol system solvents (ethanol, etc.) and the like.

The compounds of the present invention are converted into pharmacologically acceptable salts by conventionally known methods.

In addition, quaternary ammonium salt is also included in the salts. The quaternary ammonium salt means that the nitrogen atom of the compound represented by formula (I) is quaternarized by $R^0$ ($R^0$ represents C1-8 alkyl, or C1-8 alkyl substituted by phenyl).

Also, N-oxide is included in the salts. The compounds of the present invention can be made N-oxide by optional method. The N-oxide means that the nitrogen atom of the compound represented by formula (I) is oxidized.

The compounds represented by formulae (I-a) and (1-b) can be converted into cyclodextrin clathrate by the method described in the specification of JP-B-50-3362, JP-B-52-31404 or JP-B-61-52146 using α-, β- or γ-cyclodextrin or a mixture thereof. Since stability is improved and water-solubility is increased by their conversion into cyclodextrin clathrate, it is convenient when they are used as pharmaceutical preparations.

As a preferable embodiment according to this description, a preventive and/or therapeutic agent for (ischemic) organ diseases by a persistent preparation of a prostaglandin (PG) I2 agonist, an EP2 agonist or an EP4 agonist is preferable, and more preferred is a preventive and/or therapeutic agent for (ischemic) organ diseases by topical administration of a persistent preparation of a prostaglandin (PG) I2 agonist, an EP2 agonist or an EP4 agonist to an ischemic region or an injured region.

All of the PGI2 agonists so far known and PGI2 agonists which will be discovered in the future are included in the PGI2 agonist of the description.

For example, the compound represented by formula (I) or a salt thereof is preferable as the PGI2 agonist.

In addition, in formula (I),
preferred as

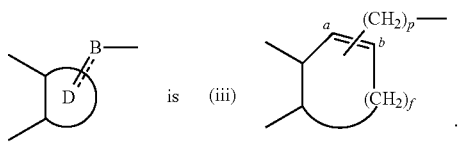

In formula (I), preferred as $R^2$ is (iii) phenyl or C4-7 cycloalkyl, (iv) 4- to 7-membered monocyclic ring containing one nitrogen atom, (v) C1-4 alkyl substituted with a benzene ring or C4-7 cycloalkyl, or (vi) C1-4 alkyl substituted with 4- to 7-membered monocyclic ring containing one nitrogen atom, and particularly preferred is (iii) phenyl or C4-7 cycloalkyl or (iv) 4- to 7-membered monocyclic ring containing one nitrogen atom.

In formula (I), preferred as $R^3$ is (ii) phenyl or C4-7 cycloalkyl, (iii) 4- to 7-membered monocyclic ring containing one nitrogen atom, (iv) C1-4 alkyl substituted with a benzene ring or C4-7 cycloalkyl, or (v) C1-4 alkyl substituted with 4- to 7-membered monocyclic ring containing one nitrogen atom, and particularly preferred is (ii) phenyl or C4-7 cycloalkyl or (iii) 4- to 7-membered monocyclic ring containing one nitrogen atom. In addition, more preferred is Compound 1

(E)-[5-[2-[1-phenyl-1-(3-pyridyl)methylideneaminoxy]ethyl]-7,8-dihydronaphthalen-1-yloxy]acetic acid

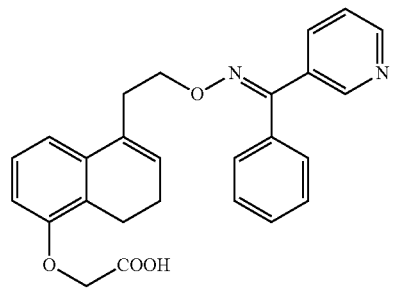 [SMILES: O=C(O)COc1cccc2c1CCC=C2CCO/N=C(\c1ccccc1)c1cccnc1]

or

Compound 2

(Z)-[5-[2-[1-phenyl-1-(3-pyridyl)methylideneaminoxy]ethyl]-7,8-dihydronaphthalen-1-yloxy]acetic acid

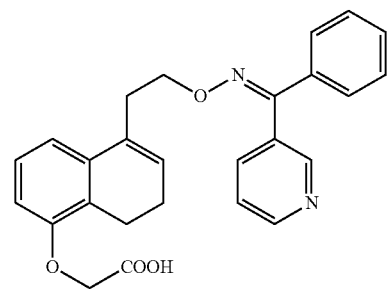 [SMILES: O=C(O)COc1cccc2c1CCC=C2CCO/N=C(/c1ccccc1)c1cccnc1]

In addition, examples of the other PGI2 agonist include beraprost sodium ((±)-(1R,2R,3aS,8bS)-2,3,3a,8b-terahydro-2-hydroxy-1-[(E)-(3S,4RS)-3-hydroxy-4-methyl-1-octen-6-ynyl]-1H-cyclopenta[b]benzofuran-5-butanoic acid sodium salt), OP-2507 (5-{(3aR,4R,6aS)-5-hydroxy-4-[(1E, 3S)-3-hydroxy-3-(cis-4-propylcyclohexyl)prop-1-enyl-3,3a, 4,5,6,6 a-hexahydrocyclopenta[b]pyrrol-2-yl}pentanoic acid methyl ester), OP-41483 ((5E)-5-[(3aS,4R,5R,6aS)-4-[(1E, 3S)-3-cyclopentyl-3-hydroxyprop-1-enyl]-5-hydroxy-hexahydropentalene-2(1H)-ylidene]pentanoic acid) and the like, and a chemically stable carbacyclin system PGI2 relate compound is preferable.

All of the EP2 agonists so far known and EP2 agonists which will be discovered in the future are included in the EP2 agonist of the description. For example, as the EP2 agonists so far known, the compounds described in JP-A-11-193268, namely the above-described compounds represented by formula (I-a), salts thereof, prodrugs thereof or cyclodextrin clathrate thereof can be cited.

Examples of the other EP2 agonist include compounds described in the specifications of WO99/33794, EP-A-974580, WO95/19964, WO98/28264, WO99/19300, EP-A-0911321, WO98/58911, U.S. Pat. No. 5,698,598, U.S. Pat. No. 6,376,533, U.S. Pat. No. 4,132,738, U.S. Pat. No. 3,965, 143 and the like.

Among the compounds represented by formula (I-a), Compound 3: (5Z,9β,11α,13E)-17,17-propano-11,16-dihydroxy-9-chloro-20-norprost-5,13-dienoic acid:

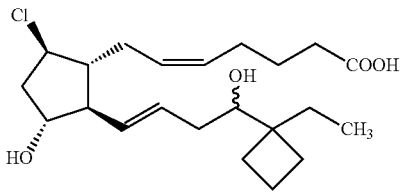 [SMILES: CCC1(C(O)C/C=C/[C@@H]2[C@@H](C/C=C\CCCC(=O)O)[C@H](Cl)C[C@H]2O)CCC1]

(the compound described in Example 17 of the specification of JP-A-11-193268), a lysine salt thereof or an α-cyclodextrin clathrate thereof, and the like can exemplified as more preferable compounds.

All of the EP4 agonists so far known and EP4 agonists which will be discovered in the future are included in the EP4 agonist of the description. For example, as the EP4 agonists so far known, the compounds described in the specification of WO00/03980, namely the above-described compounds represented by formula (I-b), salts thereof or cyclodextrin clathrate thereof can be cited.

Examples of the other EP4 agonist include compounds described in the specifications of WO99/02164, WO00/16760, WO00/18744, WO00/21542, WO00/38663, WO00/38690, WO00/38667, WO00/40248, WO00/54808, WO00/54809, WO01/10426, EP-A-1110949, EP-A-1121939, EP-A-1132086, WO200172268, JP-A-2002-104939, WO02/42268, JP-A-2002-179595, WO02/47669, WO02/64564, WO03/035064, WO03/053923, U.S. Pat. No. 6,552,067 and the like.

Among the compounds represented by formula (I-b), Compound 4: (11α,13E,15α)-9-oxo-11,15-dihydroxy-16-(3-methoxymethylphenyl)-17,18,19,20-tetranor-5-thiaprost-13-enoic acid:

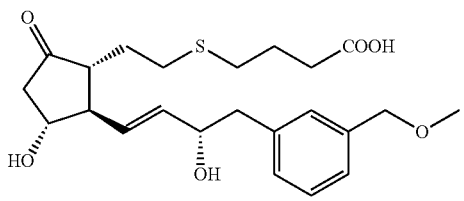 [SMILES: COCc1cccc(C[C@H](O)/C=C/[C@H]2[C@H](O)CC(=O)[C@@H]2CCSCCCC(=O)O)c1]

(the compound described in Example 3 of the specification of WO00/03980), (11α,13E,15α)-9-oxo-11,15-dihydroxy-16-(3-methoxymethylphenyl)-17,18,19,20-tetranor-5-thiaprost-13-enoic acid methyl ester and the like can exemplified as more preferable compounds.

Production Methods of Compounds According to the Present Invention:

Among the PGI2 agonists to be used in the present invention, for example, production methods of the compounds represented by formula (I) are disclosed in the specification of JP-A-6-87811.

For example, (E)-[5-[2-[1-phenyl-1-(3-pyridyl)methylideneaminoxy]ethyl]-7,8-dihydronaphthalen-1-yloxy]acetic acid (Compound 1) is described in Example 2(g).

Also, (Z)-[5-[2-[1-phenyl-1-(3-pyridyl)methylideneaminoxy]ethyl]-7,8-dihydronaphthalen-1-yloxy]acetic acid (Compound 2) is described in Example 2(f).

Production method of Beraprost ((±)-(1R,2R,3aS,8bS)-2,3,3a,8b-terahydro-2-hydroxy-1-[(E)-(3S,4RS)-3-hydroxy-4-methyl-1-octen-6-ynyl]-1H-cyclopenta[b]benzofuran-5-butanoic acid sodium salt) is disclosed in the specification of JP-A-62-134787.

Production method of OP-2507 (5-{(3aR,4R,6aS)-5-hydroxy-4-[(1E,3S)-3-hydroxy-3-(cis-4-propylcyclohexyl)prop-1-enyl-3,3a,4,5,6,6a-hexahydrocyclopenta[b]pyrrol-2-yl}pentanoic acid methyl ester) is disclosed in the specification of JP-A-61-30519.

Production method of OP-41483 ((5E)-5-[(3aS,4R,5R,6aS)-4-[(1E,3S)-3-cyclopentyl-3-hydroxyprop-1-enyl]-5-hydroxyhexahydropentalene-2(1H)-ylidene]pentanoic acid) is disclosed in the specification of JP-A-54-130543.

Production methods of the compounds represented by formula (I-a) are disclosed in the specification of JP-A-11-193268. For example, (5Z,9β,11α,13E)-17,17-propano-11,16-dihydroxy-9-chloro-20-norprost-5,13-dienoic acid (Compound 3) is described in Example 17.

Production methods of the compounds represented by formula (I-b) are disclosed in the specification of WO00/03980. For example, (11α,13E,15α)-9-oxo-11,15-dihydroxy-16-(3-methoxymethylphenyl)-17,18,19,20-tetranor-5-thiaprost-13-enoic acid (Compound 4) is described in Example 3.

Toxicity:

Since toxicity of the agents of the present invention is very low, they are sufficiently safe for using as medicine.

INDUSTRIAL APPLICABILITY

Application to Pharmaceutical Preparations:

Since the PGI2 agonist, EP2 agonist or EP4 agonist has the angiogenesis accelerating action, it is useful as preventive and/or therapeutic agents for ischemic organ diseases (e.g., arteriosclerosis obliterans, Buerger disease, Raynaud disease, cardiovascular diseases (e.g., myocardial infarction, angina pectoris, etc.), diabetic neuropathy, spinal canal stenosis, ischemic brain disease (e.g., cerebrovascular accidents, cerebral infarction, etc.), pulmonary hypertension, bone fracture, Alzheimer disease, etc.). In addition, since the PGI2 agonist, EP2 agonist or EP4 agonist has the endogenous repair factor production accelerating action, based on its action to induce differentiation from respective stem cells for repairing tissues, it is useful as preventive and/or therapeutic agents for various organ diseases (for example, liver diseases (e.g., fluminant hepatitis, acute hepatitis, hepatic cirrhosis, fatty liver, liver transplantation, etc.), kidney diseases (e.g., acute renal insufficiency, chronic renal insufficiency, etc.), lung diseases (e.g., acute pneumonia, pulmonary fibrosis, pulmonary hypertension, chronic obstructive pulmonary disease (COPD), asthma, etc.), pancreas diseases (e.g., diabetes mellitus, chronic pancreatitis, etc.), bone diseases (e.g., osteoarthritis, articular rheumatism, osteoporosis, bone fracture, periosteum injury, etc.), digestive organ diseases (e.g., gastric ulcer, duodenal ulcer, ulcerative colitis, Crohn disease, etc.), nerve degeneration diseases (e.g., stroke, Parkinson disease, Alzheimer disease, spinal canal stenosis, cerebrovascular accidents, moyamoya disease, etc.), diabetic complications (e.g., nerve disorder, skin ulcer, nephropathy, retinal disease, etc.), vascular endothelial cell diseases (e.g., restenosis after PTCA (percutaneous transluminal coronary angiopathy), arteriosclerosis, etc.), heart diseases (e.g., supraventricular tachyarrhythmia, congestive heart failure, coronary artery disease, sudden cardiomyopathy, dilated cardiomyopathy, etc.), dental diseases (e.g., periodontal disease, tooth extraction wound, oral wound, periodontal tissue disease, etc.), decubitus, glaucoma, alopecia, and the like).

As the active ingredient of the endogenous repair factor production accelerator of the present invention, one or two or more species optionally selected from the homologous group and heterogeneous group of PGI2 agonists, EP2 agonists and EP4 agonists may be used at a combination of optional ratio.

For example, PGE1, PGE2 and PGI2, derivatives thereof (e.g., 6-oxoPGE1, ornoprostil, limaprostil, enprostil, misoprostol, etc.), prodrugs thereof, persistent preparations (sustained release preparations) thereof (e.g., lipoPGE1, etc.) and endogenous inducers thereof are also included in the PGI2 agonist, EP2 agonist or EP4 agonist of the present invention, and one or two or more of them may be optionally blended and used.

The agent of the present invention may be administered as a concomitant drug in combination with other agent for (1) complementing and/or reinforcing the preventive and/or therapeutic effect of the agent of the present invention, (2) improving kinetics and absorption of the agent of the present invention and reducing its dose, and/or (3) alleviating side effects of the agent of the present invention.

The concomitant drug of the agent of the present invention with other agent may be administered in the form of a combination drug in which both components are formulated in one pharmaceutical preparation, or administered as separate pharmaceutical preparations. When administered as the separate pharmaceutical preparations, it includes simultaneous administration and differential time administration. In addition, the differential time administration may be carried out by firstly administering the agent of the present invention and then administering the other agent, or by firstly administering the other agent and then administering the agent of the present invention, and the respective administration methods mat be the same or different from each other.

The other agent may be a low molecular compound, a high molecular protein, polypeptide, polynucleotide (DNA, RNA or a gene), antisense, decoy or antibody, or a vaccine or a stem cell or the like separated from a tissue. Dose of the other agent can be optionally selected based on the clinically used dose. In addition, blending ratio of the agent of the present invention with the other agent can be optionally selected depending on the age and body weight of the subject to be administered, administration method, administration period, disease to be treated, symptoms, combination and the like. For example, from 0.01 to 100 parts by mass of the other agent may be used based on 1 part by mass of the agent of the present invention. The other agent may be administered as an optional ratio of combination of one or two or more species optionally selected from the homologous group and heterogeneous group shown in the following.

The disease in which its preventive and/or therapeutic effect is exerted by the above-described concomitant drug is not particularly limited, and it may be any disease in which the preventive and/or therapeutic effect of the agent of the present invention can be complemented and/or reinforced.

Examples of the other agent include an anti-thrombus agent, a circulation improving agent, a bronchial smooth muscle dilator, an anti-inflammatory drug, a local anesthetic, an analgesic, a bone cement, an joint lubricant, a prostaglandin derivative, an endogenous repair factor protein, an endogenous repair factor gene, various organ stem cells and the like.

Examples of the anti-thrombus agent include heparin preparations (heparin sodium, heparin calcium, dalteparin sodium, etc.), oral anticoagulants (warfarin potassium, etc.), antithrombin agents (gabexate mesylate, nafamostat mesylate, argatroban, etc.), anti-platelet agglutination inhibitors (aspirin, dipyridamole, ticlopidine hydrochloride, beraprost sodium, cilostazol, ozagrel sodium, sarpogrelate hydrochloride, ethyl eicosapentanoate, etc.), thrombolytic agents (urokinase, tisokinase, alteplase, nateplase, monteplase, pamiteplase, etc.), factor Xa inhibitors, factor VIIa inhibitors and the like.

Examples of the circulation improving agent include ifenprodil tartarate, aniracetam, donepezil hydrochloride, amantadine hydrochloride, nicergoline, ibudilast, a papaverine system, a nicotine system, a calcium antagonist, a β receptor agonist, an α receptor antagonist and the like.

Examples of the bronchial smooth muscle dilator include β 2 stimulants (e.g., ephedrine hydrochloride, isiprenali sulfate, salbutamol sulfate, tulobuterol hydrochloride, etc.), theophylline drugs (e.g., diprophylline, aminophylline, choline theophylline, etc.), or anti-choline drugs (e.g., ipratropium bromide, flutropium bromide, oxytropium bromide, etc.).

Examples of the local anesthetic include a steroid preparation, procaine, cocaine hydrochloride, lidocaine hydrochloride, ropivacaine hydrochloride and the like.

Examples of the an analgesic include non-steroidal antiinflammatory drugs (NSAID) such as aspirin, indometacin, diclofenac, meloxicam and celecoxib, opioid analgesic such as codein and morphine, pentazocine, buprenorphine hydrochloride, eptazocine hydrobromide and the like.

Examples of the bone cement include calcium phosphate and the like.

Examples of the joint lubricant include suvenyl and the like.

Examples of the prostaglandin derivative include PGE1, PGE2 and PGI2 or prodrugs thereof, lipoPGE1,6-oxoPGE1, 6-oxoPGE1 derivatives, ornoprostil, limaprostil, enptostil, misoprostol and the like.

Examples of the endogenous repair factor according to the "endogenous repair factor protein and endogenous repair factor gene" include vascular endothelial growth factor (VEGF), hepatocyte growth factor (HGF), various fibroblast growth factors (a/b FGF), transformation growth factor-β (TGF-β), platelet derived growth factor (PDGF), angiopoietin, hypoxia inducing factor (HIF), insulin-like growth factor (IGF), bone morphogenetic protein (BMP), connective tissue growth factor (CTGF) and epidermal growth factor (EGF), growth factors of their families and the like.

In addition, not only the compounds so far found but also those which will be discovered in the future are also included in the other agents capable of complementing and/or reinforcing the preventive and/or therapeutic agents of the present invention, based on the above-described mechanism.

When the agent of the present invention, or the concomitant drug of the agent of the present invention with other agent, is used for the above-described purpose, it is generally administered systemically or topically in the oral or parenteral form.

Its dose varies depending on the age, body weight, symptoms, therapeutic effect, administration method, treating period and the like, but is usually within the range of from 1 ng to 100 mg per adult per once, from once to several times a day by oral administration, or within the range of from 0.1 ng to 50 mg per adult per once, from once to several times a day, from once to several times a week, or from once to several times in 3 months by parenteral administration in the form of a persistent preparation, or continuously administered into a vein within the range of from 1 hour to 24 hours a day. Since the dose varies under various conditions as a matter of course as described above, there is a case in which a smaller dose than the above range is sufficient or a case which requires the administration exceeding the range.

When the agent of the present invention, or the concomitant drug of the agent of the present invention with other agent, is administered, it is used as solid preparations for internal use or liquid preparations for internal use for oral administration, or as injections, subcutaneous or intramuscular injections, external preparations, suppositories, eye drops, inhalations, medical device-containing preparations and the like for parental administration.

The solid preparation for internal use for use in the oral administration includes tablets, pills, capsules, powders, granules and the like. Hard capsules and soft capsules are included in the capsules.

In such a solid preparation for internal use, one or more active substances are used as such, or mixed with a filler (lactose, mannitol, glucose, microcrystalline cellulose, starch, etc.), a binder (hydroxypropylcellulose, polyvinyl pyrrolidone, magnesium aluminometasilicate, etc.), a disintegrating agent (calcium cellulose glycolate, etc.), a lubricant (magnesium stearate, etc.), a stabilizing agent, a solubilization assisting agent (glutamic acid, aspartic acid, etc.) and the like and used by making the mixture into a pharmaceutical preparation. If necessary, this may be coated with a coating agent (sucrose, gelatin, hydroxypropylcellulose, hydroxypropylmethylcellulose phthalate, etc.), or coated with two or more layers. Further capsules of an absorbable substance such as gelatin are included.

The liquid preparation for internal use for use in the oral administration includes pharmaceutically acceptable solutions, suspensions, emulsions, syrups, elixirs and the like. In such a liquid preparation, one or more active ingredient are dissolved, suspended or emulsified in a generally used diluent (purified water, ethanol, a mixed solution thereof, etc.). In addition, this liquid preparation may contain a moistening agent, a suspending agent, an emulsifying agent, a sweetener, a flavor, an aromatic, a preservative, a buffer and the like.

Dosage forms for external use for use in parenteral administration include, for example, ointments, gels, creams, fomentations, adhesive preparations, liniments, sprays, inhalations, sprays, aerosols, eye drops, nasal drops and the like. In addition, these may be sealed with a biodegradable polymer and used as medical devices (surgical suture, a bolt for use in bone fracture treatment, etc.). They contain one or more active ingredient and are prepared by a conventionally known method or based on a generally used formula.

The ointments are produced by a conventionally known method or based on a generally used formula. For example, they are prepared by suspending or melting one or more active ingredients in a base. The ointment base is selected from those which are conventionally known or generally used. For example, a single substance or a mixture of two or more substances are used, which are selected from higher fatty acids or higher fatty acid esters (adipic acid, myristic acid, palmitic acid, stearic acid, oleic acid, adipic acid ester, myristic acid ester, palmitic acid ester, stearic acid ester, oleic acid ester, etc.), waxes (beeswax, whale wax, ceresine, etc.), surfactants (polyoxyethylene alkyl ether phosphoric acid ester, etc.), higher alcohols (cetanol, stearyl alcohol, cetostearyl alcohol, etc.), silicon oil (dimethyl polysiloxane, etc.), hydrocarbons (hydrophilic vaseline, white vaseline, purified lanoline, liquid paraffin, etc.), glycols (ethylene glycol, diethylene glycol, propylene glycol, polyethylene glycol, macrogol, etc.), plant oil (castor oil, olive oil, sesame oil, turpentine oil, etc.), animal oil (mink oil, egg yolk oil, squalane, squalene, etc.), water, absorption accelerators and rash preventing agents. In addition, moisture keeping agents, preservatives, stabilizers, antioxidants, flavors and the like may be contained.

The gels are produced by a conventionally known method or based on a generally used formula. For example, they are prepared by melting one or more active ingredients in a base. The gel base is selected from those which are conventionally known or generally used. For example, a single substance or a mixture of two or more substances are used, which are selected from lower alcohols (ethanol, isopropyl alcohol, etc.), gelling agents (carboxymethyl cellulose, hydroxyethyl cellulose, hydroxypropylcellulose, ethyl cellulose, etc.), neutralizing agents (triethanolamine, diisopropanolamine, etc.), surfactants (polyethylene glycol monostearate, etc.), gums, water, absorption accelerators and rash preventing agents. In addition, preservatives, antioxidants, flavors and the like may be contained.

The creams are produced by a conventionally known method or based on a generally used formula. For example, they are prepared by melting or emulsifying one or more active ingredients in a base. The cream base is selected from those which are conventionally known or generally used. For example, a single substance or a mixture of two or more substances are used, which are selected from higher fatty acid esters, lower alcohols, hydrocarbons, polyhydric alcohols (propylene glycol, 1,3-butylene glycol, etc.), higher alcohols (2-hexyldecanol, cetanol, etc.), emulsifiers (polyoxyethylene alkyl ethers, fatty acid esters, etc.), water, absorption accelerators and rash preventing agents. In addition, preservatives, antioxidants, flavors and the like may be contained.

The fomentations are produced by a conventionally known method or based on a generally used formula. For example, they are prepared by melting one or more active ingredients in a base and then spreading and coating the resulting kneaded material on a support. The fomentation base is selected from those which are conventionally known or generally used. For example, a single substance or a mixture of two or more substances are used, which are selected from thickeners (polyacrylic acid, polyvinyl pyrrolidone, acacia, starch, gelatin, methyl cellulose, etc.), moistening agents (urea, glycerol, propylene glycol, etc.), fillers (kaolin, zinc oxide, talc, calcium, magnesium, etc.), water, solubilizing agents, tackifiers and rash preventing agents. In addition, preservatives, antioxidants, flavors and the like may be contained.

The adhesive preparations are produced by a conventionally known method or based on a generally used formula. For example, they are prepared by melting one or more active ingredients in a base and then spreading and coating the resulting material on a support. The adhesive preparation base is selected from those which are conventionally known or generally used. For example, a single substance or a mixture of two or more substances are used, which are selected from polymer bases, oils and fats, higher fatty acids, tackifiers and rash preventing agents. In addition, preservatives, antioxidants, flavors and the like may be contained.

The liniments are produced by a conventionally known method or based on a generally used formula. For example, they are prepared by dissolving, suspending or emulsifying one or more active ingredients in a single substance or two or more substances selected from water, alcohols (ethanol, polyethylene glycol, etc.), higher fatty acids, glycerol, soap, emulsifiers, suspending agents and the like. In addition, preservatives, antioxidants, flavors and the like may be contained.

In addition to the generally used diluents, the sprays and inhalations may contain stabilizers such as sodium hydrogen sulfite and buffer agents capable of giving tonicity, for example, tonicity agents such as sodium chloride, sodium citrate and citric acid. Production methods of sprays are illustratively described in, for example, U.S. Pat. No. 2,868,691 and U.S. Pat. No. 3,095,355.

Solutions, suspensions, emulsions and solid injections which are used by dissolving or suspending in a solvent prior to use are included in the injections for parenteral administration. The injections are used by dissolving, suspending or emulsifying one or more active ingredients in a solvent. These injections may be injected into a vein, an artery, muscle, under the skin, into the brain, a joint, a bone and other topical regions of organs, or directly administered using a needle-equipped blood vessel catheter or the like. As the solvent, for example, distilled water for injection, physiological saline, plant oil, alcohols such as propylene glycol, polyethylene glycol and ethanol, and combinations thereof are used. In addition, such injections may contain a stabilizer, a solubilization assisting agent (glutamic acid, aspartic acid, Polysorbate 80 (registered trade mark), etc.), a suspending agent, an emulsifying agent, a soothing agent, a buffer agent, a preservative and the like. These are produced by sterilizing at the final step or by an aseptic operation. In addition, it is possible to prepare an aseptic solid preparation, such as a freeze-dried preparation, and use it by dissolving in sterilized or aseptic distilled water for injection or other solvent prior to its use.

The eye drops for parenteral administration include an eye drop liquid, a suspension type eye drop liquid, an emulsion type eye drop liquid, a prior to use dissolution type eye drop liquid and an eye ointment.

These eye drops are produced in accordance with a conventionally known method. For example, they are used by dissolving, suspending or emulsifying one or more active ingredient in a solvent. As the solvent of eye drops, for example, sterilized purified water, physiological saline, other aqueous solvent or non-aqueous solvent for injection (e.g., plant oil, etc.) and the like and combinations thereof are used. If necessary, the eye drops may further contain substances optionally selected from tonicity agents (sodium chloride, concentrated glycerol, etc.), buffer agents (sodium phosphate, sodium acetate, etc.), surfactants (Polysorbate 80 (registered trade mark), polyoxyl 40 stearate, polyoxyethylene hardened castor oil, etc.), stabilizers (sodium citrate, sodium edetate, etc.), antiseptics (benzalkonium chloride, paraben, etc.) and the like. These are produced by sterilizing at the final step or by an aseptic operation. In addition, it is possible to prepare an aseptic solid preparation, such as a freeze-dried preparation, and use it by dissolving in sterilized or aseptic distilled purified water or other solvent prior to its use.

As the inhalations for parenteral administration, aerosols, powders for inhalation or solutions for inhalation are included, and said solutions for inhalation may be in a form which is used by dissolving or suspending in water or other appropriate solvent prior to its use.

These inhalations are produced in accordance with conventionally known methods.

For example, in the case of solutions for inhalation, they are prepared by optionally selecting antiseptics (benzalkonium chloride, paraben, etc.), coloring agents, buffer agents (sodium phosphate, sodium acetate, etc.), tonicity agents (sodium chloride, concentrated glycerol, etc.), thickeners (carboxyvinyl polymer, etc.), absorption accelerators and the like, if necessary.

In the case of powders for inhalation, they are prepared by optionally selecting lubricants (stearic acid and a salt thereof, etc.), binders (starch, dextrin, etc.), fillers (lactose, cellulose, etc.), coloring agents, antiseptics (benzalkonium chloride, paraben, etc.), absorption accelerators and the like, if necessary.

When solutions for inhalation are administered, a sprayer (atomizer or nebulizer) is generally used, and an inhalation administering device for powders is generally used when powders for inhalation are used.

As other compositions for parenteral administration, suppositories for rectal administration, pessaries for vaginal administration and the like are included, which contain one or more active ingredients and are formulated in the usual way.
Application to Topical Regions:

As the topical administration of the present invention, the administration method is not particularly limited, so long as the agent of the present invention or a concomitant drug of the agent of the present invention with other agent can be topically supplied to regions of a disease. Its examples include injections and embedding agents to be used in muscle, under the skin, and in the skin, blood vessel, heart muscle, alveoli, joint part, vertebra, bone part, tooth root part, injured organ and the like, medical device-containing preparations in which the agent of the present invention or a concomitant drug of the agent of the present invention with other agent is contained in a medical device (stent, fixing bolt, fixer, thread, etc.), or coating agents coated with the same, solid preparations such as granules and powders, adhesive preparations, gels, ointments, films, preparation enclosed in a biodegradable polymer, or enclosed medical devices and the like.

As the persistent preparation of the present invention, the pharmaceutical preparation is not limited, so long as the active ingredient can be persistently supplied to a region of a disease. Its examples include sustained release injections (e.g., microcapsule preparations, microsphere preparations, nanosphere preparations, etc.), embedding preparations (e.g., film preparations, etc.), ointments, coatings in which the active ingredient is contained or coated in a medical device (stent, fixing bolt, fixer, suture, etc.).

The microcapsule preparations, microsphere preparations and nanosphere preparations of the present invention are fine particle pharmaceutical composition with a biodegradable polymer, which contains an active ingredient as the active ingredient.

A bioabsorbable polymer is present in the sustained drug release system of the present invention, which is achieved by a natural polymer or a synthetic polymer. The mechanism for controlling the rate of sustained release therefrom includes a degradation controlling type, a dispersion controlling type, a membrane permeation controlling type or the like.

Examples of the natural polymer as the bioabsorbable polymer of the present invention include plant-produced polysaccharides (e.g., cellulose, starch, alginic acid, etc.), animal-produced polysaccharides and proteins (e.g., chitin, chitosan, collagen, gelatin, albumin, glycosaminoglycan, etc.) and microorganism-produced polyesters and polysaccharides (e.g., poly-3-hydroxyalkanoate, hyaluronic acid, etc.).

Also, examples of the biodegradable polymer include fatty acid ester polymers or copolymers thereof, polyacrylic acid esters, polyhydroxybutyric acids, polyalkylene oxalates, polyortho esters, polycarbonate and polyamino acids, which can be used alone or as a mixture thereof. Examples of the fatty acid ester polymers or copolymers thereof include polylactic acid, polyglycolic acid, polycitric acid, polymalic acid, polyethylene succinate, polybutylene succinate, poly-ε-caprolactone, polybutylene terephthalate adipate or lactic acid-glycolic acid copolymer, which can be used alone or as a mixture thereof. In addition to these, poly α-cyano acrylic acid ester, poly-β-hydroxy butyric acid, polytrimethylene oxate, polyortho ester, polyortho carbonate, polyethylene carbonate, poly-γ-benzyl-L-glutamic acid, polyvinyl alcohol, polyester carbonate, polyacid anhydride, polycyano acrylate, polyphosphazine or poly-L-alanine can be used alone or as a mixture thereof. Preferred is polylactic acid, polyglycolic acid or a lactic acid-glycolic acid copolymer, and more preferred is a lactic acid-glycolic acid copolymer.

Average molecular weight of these biodegradable high molecular weight polymers to be used in the present invention is preferably from about 2,000 to about 800,000, more preferably from about 5,000 to about 200,000. For example, in the case of polylactic acid, its weight average molecular weight is preferably from about 5,000 to about 100,000. It is more preferably from about 6,000 to about 50,000. Polylactic acid can be synthesized in accordance with the conventionally known production method. In the case of the lactic acid-glycolic acid copolymer, its compositional ratio of lactic acid and glycolic acid preferably from about 100/0 to about 50/50 (w/w), particularly preferably from about 90/10 to about 50/50 (w/w). Weight average molecular weight of the lactic acid-glycolic acid copolymer is preferably from about 5,000 to about 100,000. It is more preferably from about 10,000 to about 80,000. The lactic acid-glycolic acid copolymer can be synthesized in accordance with the conventionally known production method. In addition, in order to control initial burst, basic amino acids (e.g., alginic acid, etc.) may be added.

According to the description, the weight average molecular weight is a polystyrene-based molecular weight measured by a gel permeation chromatography (GPC).

The above-described biodegradable high molecular weight polymer can be changed depending on the strength of pharmacological activity of the active ingredient and the drug release of interest, so long as the object of the present invention is attained, and for example, it is used in an amount of from about 0.2 to about 10,000 times (weight ratio), preferably from about 1 to about 1,000 times (weight ratio), more from about 1 to about 100 times (weight ratio), based on said physiologically active substance.

The microspheres, microcapsules and nanocapsules of the present invention can be produced for example by a submerged drying method (e.g., o/w method, w/o method, w/o/w method, etc.), a phase separation method, a spray drying method, a supercritical fluid granulation method or a method corresponding thereto.

Specific production methods on the submerged drying (o/w method) and spray drying are described in the following.

(1) In the submerged drying method (o/w method), an organic solvent solution of a biodegradable polymer is firstly prepared. It is preferable that the organic solvent to be used in producing the microspheres, microcapsules and nanocapsules of the present invention has a boiling point of 120° C. or less. Examples of the organic solvent include halogenated hydrocarbons (e.g., dichloromethane, chloroform, etc.), aliphatic esters (e.g., ethyl acetate, etc.), ethers, aromatic hydrocarbons, ketones (acetone, etc.) and the like. Two or more of them may be used by mixing at an optional ratio. Desirable organic solvent is dichloromethane or acetonitrile. The organic solvent is preferably dichloromethane. Concentration of the biodegradable polymer in the organic solvent solution varies depending on the molecular weight of the biodegradable polymer, kind of the organic solvent and the like, but is generally selected within the range of from about 0.01 to about 80% (v/v). It is preferably from about 0.1 to about 70% (v/v), more preferably from about 1 to about 60% (v/w).

An active ingredient is added to and dissolved in the thus obtained organic solvent solution of biodegradable polymer. Amount of this active ingredient to be added varies depending on the kind of agent, angiogenesis action, effect-persisting period of time and the like, but is from about 0.001% to about 90% (w/w), preferably from about 0.01% to about 80% (w/w), more preferably from about 0.3% to 30% (w/w), as concentration of the biodegradable high molecular polymer in the organic solvent solution.

Next, the thus prepared organic solvent solution is further added to a water phase to form an o/w emulsion using a stirrer, emulsifier or the like. The water phase volume in this case is selected generally from about 1 time to about 10,000 times of the oil phase volume. This is selected more preferably from about 2 times to about 5,000 times. This is selected particularly preferably from about 5 times to about 2,000 times. An emulsifying agent may be added to the water phase of the above-described outer phase. The emulsifying agent may be any agent which can generally form a stable o/w emulsion. Examples of the emulsifying agent include an anionic surfactant, a nonionic surfactant, a polyoxyethylene castor oil derivative, polyvinyl pyrrolidone, polyvinyl alcohol, carboxymethylcellulose, lecithin, gelatin and the like. These may be used in an optional combination. Concentration of the emulsifying agent in the outer water phase is preferably from about 0.001% to about 20% (w/w). It is more preferably from about 0.01% to about 10% (w/w), particularly preferably from about 0.05% to about 5% (w/w).

A generally used method is employed for the evaporation of solvent in the oil phase. The method is carried out under ordinary pressure or gradually reducing the pressure while stirring using a stirrer, magnetic stirrer or the like, or using a rotary evaporator or the like while adjusting the degree of vacuum. After fractionating the thus obtained microspheres by centrifugation or filtration, the free active ingredient, emulsifying agent and the like adhered to the micro sphere surface are washed several times repeatedly with, for example, a surfactant solution, an alcohol or the like, and the resulting microspheres are again dispersed in distilled water or a dispersion medium containing a filler (mannitol, sorbitol, lactose, etc.) or the like and freeze-dried. As the above-described o/w method, microspheres may be produced by a method in which an active ingredient is dispersed in an organic solvent solution of biodegradable polymer, namely an s/o/w method.

(2) When microspheres are produced by a spray drying method, an organic solvent in which a biodegradable polymer and an active ingredient are dissolved, or an emulsion of the same, is sprayed into a drying chamber of a spray dryer device (spray dryer) using a nozzle, and the organic solvent or water in the fine particle droplets is evaporated within a extremely short period of time to prepare microspheres. As the nozzle, there are a double fluid nozzle type, a pressure nozzle type, a rotary disc type and the like. In this case, for the purpose of preventing aggregation of microspheres, if necessary, it is effective to spray an organic solvent or aqueous solution of an aggregation preventing agent (mannitol, lactose, gelatin, etc.) through another nozzle, simultaneously with the spraying of o/w emulsion. As the thus obtained microspheres, more complete removal of water and solvent in the microspheres is carried out under a reduced pressure, with heating, if necessary.

Examples of the film preparations include those in which the above-described biodegradable polymer and active ingredient are dissolved in an organic solvent and then evaporated into dryness to form a film or in which the biodegradable polymer and active ingredient are dissolved in an appropriate solvent and then gelatinized by adding a granulation agent (celluloses, polycarbonates, etc.).

The microspheres, microcapsules and nanospheres of the present invention can be made into various dosage forms of pharmaceutical preparation, for example, as such, or using a spherical, rod, needle, bolt, filamentous, pellet, film or cream-shaped pharmaceutical composition as the material substance.

In addition, using this pharmaceutical preparation, it can be administered as parenteral preparations for topical administration (e.g., injections and embedding agents to be used in muscle, under the skin, and in the skin, heart muscle, abdominal cavity, bronchus, blood vessel, alveoli, injured region of vascular endothelium, brain, marrow, inside of dura mater, outside of dura mater, joint part, vertebra, bone part, periodontal part, various organs and the like, solid preparations such as granules and powders, liquid preparations such as suspensions, adhesive preparations, film preparations, ointments, medical device-containing preparations in which the active ingredient is contained in a medical device (stent, bolt, suture thread, etc.), coating agents coated with the same, and the like). In addition, it can be directly administered into, for example, an ischemic region of heart muscle using blood vessel catheter or the like.

For example, when microspheres are made into injections, practical pharmaceutical preparations for injection can be obtained by making the microspheres into aqueous suspensions together with a dispersing agent, a preservative, a tonicity agent, a buffer agent, a pH adjusting agent and the like. Also, they are made into injections which can be practically used as oily suspensions by dispersing together with a plant oil or its mixture with phospholipid such as lecithin, or a middle chain fatty acid triglyceride (e.g., Migliol 812, etc.).

Particle size of the microspheres, for example when used as suspension injections, may be within such a range that their dispersing degree and through-needle property are satisfied, and a range of from about 0.1 to about 300 μm as the average particle size can be exemplified. It is preferably within the range of from about 1 to 150 μm, more preferably a particle size of within the range of from about 2 to 100 μm. As described above, it is preferable that the pharmaceutical composition of the present invention is a suspension. It is preferable that the pharmaceutical composition of the present invention is in the form of fine particles. This is because the pharmaceutical composition does not give patients too excess pain when administered through a needle which is used for usual subcutaneous or intramuscular injection. The pharmaceutical composition of the present invention is particularly preferable as injections. When the microspheres are made into sterile preparations, a method in which the entire production steps are carried out under aseptic conditions, a method in which they are sterilized with gamma rays, a method in which an antiseptic is added and the like can be employed, Although not particularly limited.

The action of the active ingredient of the pharmaceutical composition of the present invention has a sustained release property, and the sustained release period varies depending on the kind, blending amount and the like of the biodegradable polymer, it has a sustained release period of generally from 1 week to 3 months, so that it can be used as a stem cell differentiation induction accelerator or an angiogenesis accelerator by accelerating production of various endogenous repair factors in (ischemic) organ disease regions.

Although dose of the pharmaceutical composition of the present invention varies depending on the kind and content of the active ingredient, dosage forms, persisting period of time of the drug release, the animal to be administered and the like, it may be an effective amount of the active ingredient. For example, when the composition is used as microspheres in an ischemic region, it may be administered at a dose of from about 0.001 mg to 500 mg, preferably from about 0.01 mg to 50 mg, per once, as the active component per adult (50 kg in body weight), from once a day to once in 3 months.

In addition, for the coldness, numbness, intermittent claudication, pain at rest, skin ulcer or the like on the limbs in the case of ASO, Buerger disease, diabetic neuropathy or the like, it is preferable to carry out intramuscular administration of the agent of the present invention or its persistent preparation, for example, to the diseased region or the vicinity thereof continuously for a period of approximately from once a day to 4 weeks.

For myocardial infarction, angina pectoris and the like, it is preferable to directly carry out intramuscular administration of the agent of the present invention or its persistent preparation, for example, to the ischemic heart muscle region or the vicinity thereof, and it is preferable to carry out the administration directly under thoracotomy or using a needle-equipped blood vessel catheter or the like. As the administration period, it is preferable to carry out the intramuscular administration continuously, for example, for a period of approximately from once a day to 4 weeks.

In the case of osteoporosis, periodontal tissue damage, bone fracture, osteoarthritis and the like, it is preferable to administer the agent of the present invention or its persistent preparation alone, or by mixing it with a bone cement, a joint lubricant, a prosthetic tool or the lie, topically to the diseased region or the vicinity thereof.

In the case of pulmonary hypertension, COPD and the like, it is preferable to carry out inhalation of the agent of the present invention or its persistent preparation as solutions for inhalation or powders for inhalation.

BEST MODE FOR CARRYING OUT THE INVENTION

Figure 1:
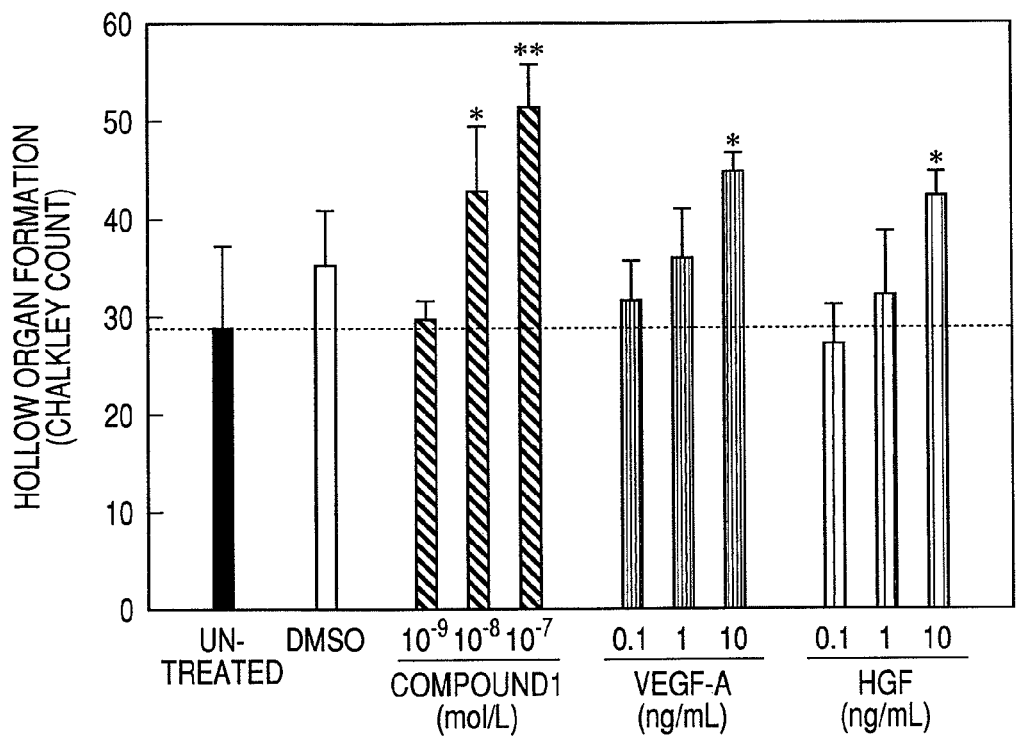
FIG. 1 shows a measured result of hollow organ formation acceleration action of Compound 1 ((E)-[5-[2-[1-phenyl-1-(3-pyridyl)methylideneaminoxy]ethyl]-7,8-dihydronaphthalen-1-yloxy]acetic acid).

Pharmacological tests are shown in the following as the examples of the present invention, but these are for thoroughly understanding the present invention and do not limit the scope of the present invention. In this connection, improvement of measuring accuracy and modification of measuring sensitivity were applied as follows to the measuring methods for evaluating the compounds of the present invention.

Example 1

Measurement of Angiogenesis Acceleration Action (In Vitro)

Test Method:

An angiogenesis kit (manufactured by Kurabo; constituted from normal human umbilical cord vein vascular endothelial cells and normal human skin fibroblasts) was cultured for 3 hours, and then the culture medium (the medium for angiogenesis use attached to the angiogenesis kit was used as the culture medium and cultured at 37° C. under a moist environment of 5% carbon dioxide-95% air, and a carbon dioxide incubator BNA-121D was used as the incubator) was changed and an agent to be tested was added to each well (0.5 ml/well). The medium exchange was carried out also on the 3rd, 6th and 8th days after commencement of the culturing and the fresh agent to be tested was added. The kind and concentration of the agent to be tested were untreated, solvent (DMSO) 0.1%, Compound 1 $10^{-9}$, $10^{-8}$ and $10^{-7}$ mol/l, VEGF-A 0.1, 1 and 10 ng/ml and HGF 0.1, 1 and 10 ng/ml, and the culturing was carried out by using 3 wells for each concentration. Fixation was carried out 10 days after the commencement of culturing, and staining of hollow organ with anti-CD31 antibody was carried out by using a hollow organ staining kit (manufactured by Kurabo). As the evaluation, Chalkley Grid (a grid lens, manufactured by Kurabo) was mounted on the eyepiece of a microscope, and the hollow organ formation was evaluated by counting intersections of the randomly arrange points of Chalkley Grid with the formed hollow organ (by referring to the evaluation method of *J. Pathol.*, 177, 275-283 (1995)). The counting was carried out at 12 positions per well, and the total was calculated.

As the agent to be tested, Compound 1 ((E)-[5-[2-[1-phenyl-1-(3-pyridyl)methylideneaminoxy]ethyl]-7,8-dihydronaphthalen-1-yloxy]acetic acid) was dissolved in dimethyl sulfoxide (DMSO) to prepare $10^{-4}$, $10^{-5}$ and $10^{-6}$ mol/l solutions which were then used by diluting 1/1000 time with the culture medium.

As the VEGF-A (vascular endothelial growth factor-A), the 2 µg/ml solution of VEGF contained in the angiogenesis control reagent kit of Kurabo was diluted with the culture medium and used.

As the HGF (human hepatocyte growth factor), the 5 µg/ml solution of HGF purchased from R & D System-Funakoshi was diluted with the culture medium and used.

Statistical Analysis Method:

The counts of hollow organ formation in the untreated wells were compared with those of the wells treated with respective concentrations of test samples by Dunnett's test (two-sided test). The significance level was set to 5%.

In this connection, the data were shown by average value of 3 wells and standard deviation.

The test results are shown in FIG. 1.

Results:

Compound 1 accelerated hollow organ formation statistically significantly by $10^{-8}$ and $10^{-7}$ mol/l. In addition, the VEGF-A and HGF accelerated hollow organ formation at a concentration of 10 ng/ml. Based on the above results, it was revealed that Compound 1 has an angiogenesis accelerating effect having a strength equivalent to the positive control agents VEGF-A and HGF in a co-culture system of human vascular endothelial cells and human fibroblasts.

Example 2

Measurement of Endogenous Repair Factor (HGF, VEGF) Protein Producing Action (In Vitro)

Test Method:

An angiogenesis kit (manufactured by Kurabo; constituted from normal human umbilical cord vein vascular endothelial cells and normal human skin fibroblasts) was cultured for 3 hours, and then the culture medium (the medium for angiogenesis use attached to the angiogenesis kit was used as the culture medium and cultured at 37° C. under a moist environment of 5% carbon dioxide-95% air, and a carbon dioxide incubator BNA-121D was used as the incubator) was changed and an agent to be tested was added to each well (0.5 ml/well). The agent to be tested were solvent (DMSO) 0.1% and Compound 1 $10^{-7}$ mol/l, and the culturing was carried out by using 3 wells for each. Culture supernatants were collected before commencement of the culturing and 1, 2, 6, 24, 48 and 72 hours after the commencement. HGF and VEGF protein concentrations in the culture supernatants were measured by using an ELISA kit (R % D system-Funakoshi).

As the agent to be tested, Compound 1 ((E)-[5-[2-[1-phenyl-1-(3-pyridyl)methylideneaminoxy]ethyl]-7,8-dihydronaphthalen-1-yloxy]acetic acid) was dissolved in dimethyl sulfoxide (DMSO) to prepare $10^{-4}$ mol/l solution which was then used by diluting 1/1000 time with the culture medium.

Statistical Analysis Method:

Results of the solvent control wells were compared with those of the wells treated with the agent to be tested by Dunnett's test (two-sided test). The significance level was set to 5%.

In this connection, the data were shown by average value of 3 wells and standard deviation.

The test results after 72 hours of the culturing are shown in Table 1.

TABLE 1

| Agent tested | HGF (pg/ml) | VEGF (pg/ml) |
| --- | --- | --- |
| Solvent control (DMSO) | 110 ± 16 | 2004 ± 76 |
| Compound 1 | 518 ± 15*** | 3034 ± 30*** |

***p < 0.001 vs. solvent control

Results:

Compound 1 accelerated production of HGF protein and VEGF protein statistically significantly in comparison with the solvent control, by 72 hours of culturing at a concentration of $10^{-7}$ mol/l.

Example 3

Production of Persistent Preparations

Preparation Example 1

A dichloromethane (1 ml) solution of 100 mg of a polylactic acid-glycolic acid copolymer (hereinafter referred to as "PLGA") (polylactic acid:glycolic acid=1:1 (mol %), weight average molecular weight 40,000, PLGA5-1, manufactured by Mitsui Kagaku) and Compound 1 (5 mg) was prepared. An O/W emulsion was prepared by adding the solution prepared in the above to 300 ml of 0.1% polyvinyl alcohol (Nacalai Tesque) aqueous solution (pH 3.0, adjusted with 1 N hydrochloric acid) which was stirred at 5,000 rpm using TK Robomix (Tokushu Kiki, MARK II 2.5 type), and stirring the mixture at room temperature for 3 minutes. This O/W emulsion was stirred at room temperature for 2 hours to evaporate dichloromethane, and the oil phase was solidified and then centrifuged at 3,000 rpm for 10 minutes using a centrifuge (Hitachi, O5PR-22). The supernatant was discarded, and the residue was dispersed in distilled water for injection (35 ml) and then centrifuged at 3,000 rpm for 10 minutes using the centrifuge. The supernatant was discarded, and the residue was dispersed in 0.2% Tween 80 solution (35 ml) and then centrifuged at 3,000 rpm for 10 minutes using the centrifuge. The supernatant was discarded, and the residue was dispersed in distilled water for injection (35 ml) and then again centrifuged at 3,000 rpm for 10 minutes using the centrifuge. Finally discarding the supernatant, the precipitate was soaked in dry ice-methanol, frozen and then dried under a reduced pressure, thereby producing a microsphere preparation of Compound 1.

Preparation Example 2

A dichloromethane (1 ml) solution of 100 mg of a polylactic acid-glycolic acid copolymer (hereinafter referred to as "PLGA") (polylactic acid:glycolic acid=1:1 (mol %), weight average molecular weight 20,000, PLGA5020, Wako Pure Chemical Industries) and Compound 1 (5 mg) was prepared. Thereafter, the same operation of Preparation Example 1 was carried out to produce a microsphere preparation of Compound 1.

Preparation Example 3

A dichloromethane (3 ml) solution of 100 mg of a polylactic acid-glycolic acid copolymer (to be referred to as PLGA hereinafter) (polylactic acid:glycolic acid=1:1 (mol %), weight average molecular weight 40,000, PLGA5-1, manufactured by Mitsui Kagaku) and Compound 1 (5 mg) was prepared. Thereafter, the same operation of Preparation Example 1 was carried out to produce a microsphere preparation of the Compound 1.

Preparation Test Example 1

Measurement of Inclusion Efficiency

The microspheres produced in Preparation Examples 1, 2 and 3 (respectively about 10 mg) were mixed with an acetonitrile solution containing an appropriate internal standard and dissolved by carrying out an ultrasonic treatment. Compound 1 content of each of the solutions was measured by a high performance liquid chromatography, and inclusion efficiency of Compound 1 in the microsphere was calculated by the following formula.

Inclusion efficiency(%)=(content found/content calculated)×100

As a result, the microsphere preparation of Preparation Example 1 showed an inclusion efficiency of 70.9%, the microsphere preparation of Preparation Example 2 showed an inclusion efficiency of 100% and the microsphere preparation of Preparation Example 3 showed an inclusion efficiency of 74.3%.

Preparation Test Example 2

In Vitro Release Test

Each of the microsphere preparations produced in Preparation Examples 1, 2 and 3 was added to 0.2% Tween 80 1/15 M phosphate buffer pH 6.8 to a concentration of 100 μg/ml as the agent and uniformly dispersed by ultrasonic treatment using Vortex. This was dispensed at 1 ml into containers and put into a 37° C. constant temperature oven. The containers were periodically sampled out and centrifuged at 12,000 rpm for 5 minutes, and the residual amount of Compound 1 in microspheres of the pellet was measured by a high performance liquid chromatography (HPLC).

Figure 2:
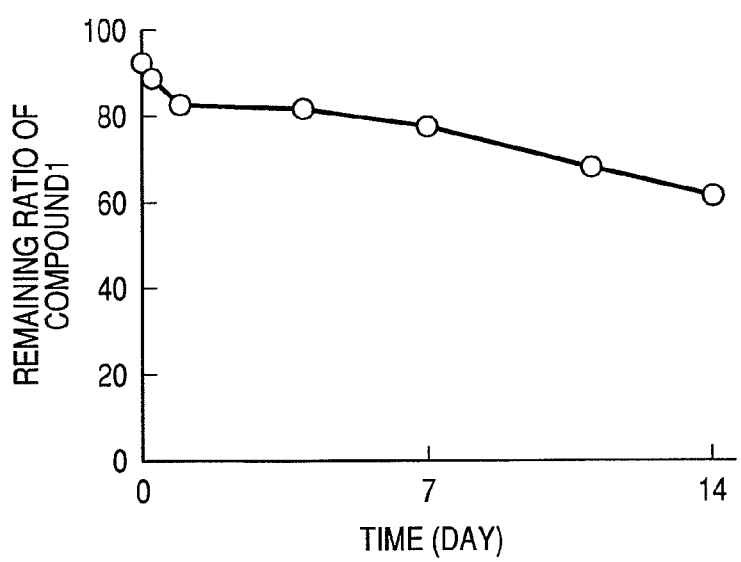
FIG. 2 shows a release test result of the microsphere preparation produced in Preparation Example 1.
Figure 3:
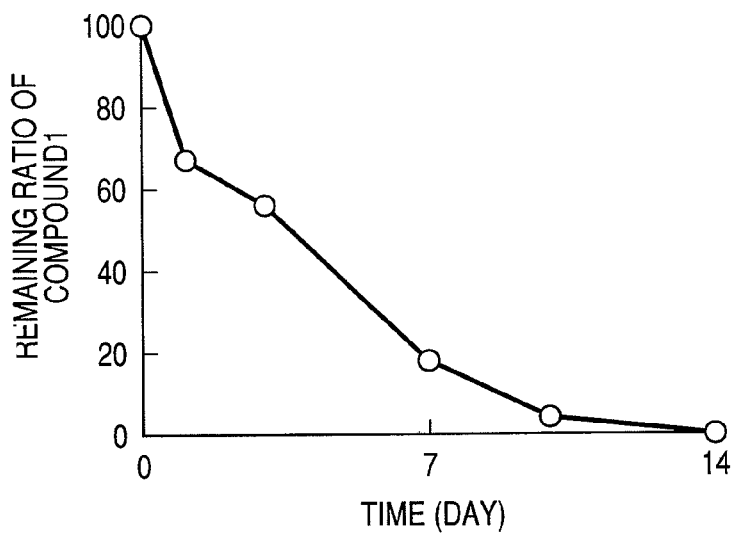
FIG. 3 shows a release test result of the microsphere preparation produced in Preparation Example 2.
Figure 4:
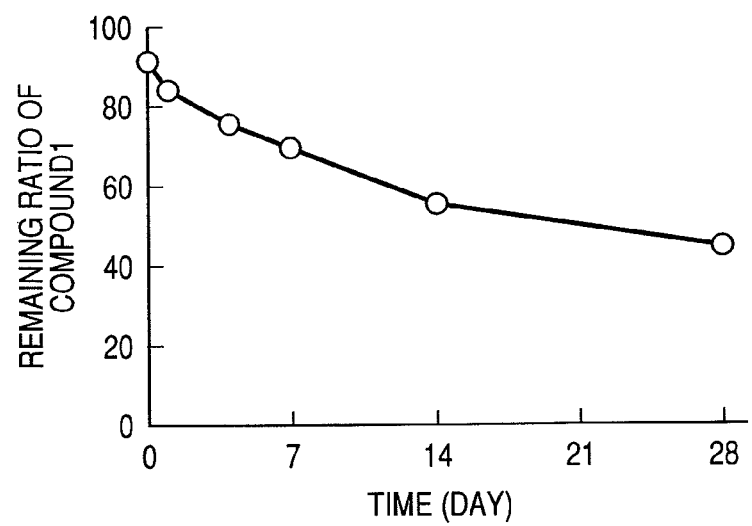
FIG. 4 shows a release test result of the microsphere preparation produced in Preparation Example 3.

Results of the microsphere preparation produced in Preparation Example 1 are shown in FIG. 2, and results of the microsphere preparation produced in Preparation Example 2 in FIG. 3, and results of the microsphere preparation produced in Preparation Example 3 in FIG. 4.

In this connection, the residual ratio in FIGS. 2, 3 and 4 means a ratio of Compound 1 remaining in microspheres to the initial.

As a result, the microsphere preparation of Preparation Example 1 released about 40% of the agent during 14 days, and the microsphere preparation of Preparation Example 2 released the whole amount during about 10 days. The microsphere preparation of Preparation Example 3 released about 60% during 28 days.

Example 4

Angiogenesis Test (In Vivo Test) Using Rat Leg Ischemia (Arteriosclerosis Obliterans (ASO)) Model Leg ischemia model was prepared by ligating rat left femoral artery. Blood flow in hind legs was measured by using Laser Doppler Imager (Moor Instruments) 2 weeks after the preparation, and the animals were divided into 6 groups (n=5) in such a manner that the average value of blood flow became almost uniform.

Starting on the next day of the grouping, 0.1 ml/site, 2 sites, of the agent to be tested was administered by intramuscular injection into the left femoral adductor, for once a week, 4 times in total as a solution to be tested. One week after completion of the final administration, blood flows of hind legs were measured by using Laser Doppler Imager (Moor Instruments), and blood flows of the treated leg (left leg) and untreated leg (right leg) were compared and examined. The results of treated leg/untreated leg (%) are shown in Table 2.

In this connection, construction of the solution to be tested is as follows. Solvent (control) group: 0.2 w/v % Tween 80 solution (0.2 ml).

Polymer Group:
  The polylactic acid-glycolic acid copolymer used in Preparation Example 2 was suspended in 0.2 w/v % Tween 80 solution (0.2 ml). In this connection, amount of the polylactic acid-glycolic acid copolymer is identical to the amount contained in the Compound 1 MS (1 mg).

Compound 1 (1 mg) Group:
  Compound 1 (1 mg) was suspended in 0.2 w/v % Tween 80 solution (0.2 ml).

Compound 1 MS (0.01 mg) Group:
  The microsphere preparation produced in Preparation Example 2 containing 0.01 mg of Compound 1 was suspended in 0.2 w/v % Tween 80 solution (0.2 ml).

Compound 1 MS (0.1 mg) Group:
  The microsphere preparation produced in Preparation Example 2 containing 0.1 mg of Compound 1 was suspended in 0.2 w/v % Tween 80 solution (0.2 ml).

Compound 1 MS (1 mg) Group:
  The microsphere preparation produced in Preparation Example 2 containing 1 mg of Compound 1 was suspended in 0.2 w/v % Tween 80 solution (0.2 ml).

TABLE 2

| Solution to be tested | Treated leg/untreated leg blood flow ratio (%) |
|---|---|
| Control | 67.3 ± 5.1 |
| Polymer | 68.7 ± 4.1 |
| Compound 1 (1 mg) | 76.2 ± 2.8**## |
| Compound 1 MS (0.01 mg) | 74.0 ± 7.1 |
| Compound 1 MS (0.1 mg) | 78.3 ± 4.6**## |
| Compound 1 MS (1 mg) | 89.0 ± 4.4**##$$ |

**significant difference from Control at $p < 0.01$ (Student's t-test)
significant difference from Polymer at $p < 0.01$ (Student's t-test)
$$significant difference from Compound 1 (1 mg) at $p < 0.01$ (Student's t-test)

Results:

Although significant recovery of blood flow against Control was found even by the administration of Compound 1 (1 mg) alone, further stronger blood flow improving effect than Compound 1 (1 mg) was observed by the administration of the microsphere (MS) preparation (Preparation Example 2) of Compound 1.

In comparison with the polymer group, dose-correlative blood flow improving effect was found in Compound 1 MS preparation, and significant blood flow improving effect action was found in Compound 1 MS (0.1 mg) and Compound 1 MS (1 mg).

Example 5

Angiogenesis Test Using Rat Leg Ischemia (Arteriosclerosis Obliterans (ASO)) Model; Determination of Minimum Effective Dose (In Vivo Test)

Leg ischemia model was prepared by ligating rat left femoral artery. Blood flow in hind legs was measured by using Laser Doppler Imager (Moor Instruments) 1 week after the preparation, and the animals were divided into 4 groups (n=5) in such a manner that the average value of blood flow became almost uniform.

Starting on the next day of the grouping, 0.1 ml/site, 2 sites, of the agent to be tested was administered by intramuscular injection into the left femoral adductor (polymer group, Compound 1 MS group), for once a week, 4 times in total as a solution to be tested. One week after completion of the final administration, blood flows of hind legs were measured by using Laser Doppler Imager (Moor Instruments), and blood flows of the treated leg (left leg) and untreated leg (right leg) were compared and examined. The results of treated leg/untreated leg (%) are shown in Table 3.

In this connection, construction of the solution to be tested is as follows.

Polymer Group:
  The polylactic acid-glycolic acid copolymer used in Preparation Example 2 was suspended in 0.2 w/v % Tween 80 solution (0.2 ml). In this connection, amount of the polylactic acid-glycolic acid copolymer is identical to the amount contained in Compound 1 MS (0.1 mg).
Compound 1 MS (0.03 mg) Group:
  The microsphere preparation produced in Preparation Example 2 containing 0.03 mg of Compound 1 was suspended in 0.2 w/v % Tween 80 solution (0.2 ml).
Compound 1 MS (0.1 mg) Group:
  The microsphere preparation produced in Preparation Example 2 containing 0.1 mg of Compound 1 was suspended in 0.2 w/v % Tween 80 solution (0.2 ml).
Compound 1 MS (0.3 mg) Group:
  The microsphere preparation produced in Preparation Example 2 containing 0.3 mg of Compound 1 was suspended in 0.2 w/v % Tween 80 solution (0.2 ml).

TABLE 3

| Solution to be tested | Treated leg/untreated leg blood flow ratio (%) |
| --- | --- |
| Polymer | 57.3 ± 4.5 |
| Compound 1 MS (0.03 mg) | 65.1 ± 3.7* |
| Compound 1 MS (0.1 mg) | 68.4 ± 3.2** |
| Compound 1 MS (0.3 mg) | 72.7 ± 4.6** |

*p < 0.05 vs. Polymer (Student's t-test)
**p < 0.01 vs. Polymer (Student's t-test)

Results:

In comparison with the polymer group, dose-correlative blood flow improving effect was found in the microsphere (MS) preparation of Compound 1, and significant blood flow improving effect action was found in Compound 1 MS (0.03 mg). This, since significant blood flow improving effect action was not found in Compound 1 MS (0.01 mg) in Example 4, it was suggested that the minimum effective dose is 0.03 mg.

Example 6

Angiogenesis Test Using Rat Leg Ischemia (Arteriosclerosis Obliterans (ASO)) Model; Usefulness of Topical Administration (In Vivo Test)

Leg ischemia model was prepared by ligating rat left femoral artery. Blood flow in hind legs was measured by using Laser Doppler Imager (Moor Instruments) 1 week after the preparation, and the animals were divided into 4 groups (n=5) in such a manner that the average value of blood flow became almost uniform.

Starting on the next day of the grouping, 0.1 ml/site, 2 sites, of the agent to be tested was administered by intramuscular injection into ischemic regions of the left femoral adductor (polymer group, Compound 1 group, Compound 1 MS group) and normal region of the right shoulder upper arm (Compound 1 MS group), for once a week, 4 times in total as a solution to be tested. One week after completion of the final administration, blood flows of hind legs were measured by using Laser Doppler Imager (Moor Instruments), and blood flows of the treated leg (left leg) and untreated leg (right leg) were compared and examined. The results of treated leg/untreated leg (%) are shown in Table 4.

In this connection, construction of the solution to be tested is as follows.

Polymer Group:
  The polylactic acid-glycolic acid copolymer used in Preparation Example 2 was suspended in 0.2 w/v % Tween 80 solution (0.2 ml). In this connection, amount of the polylactic acid-glycolic acid copolymer is identical to the amount contained in Compound 1 MS (1 mg).
Compound 1 (0.1 mg) Group:
  Compound 1 (0.1 mg) was suspended in 0.2 w/v % Tween 80 solution (0.2 ml).
Compound 1 MS (0.1 mg) Group:
  The microsphere preparation produced in Preparation Example 2 containing 0.1 mg of Compound 1 was suspended in 0.2 w/v % Tween 80 solution (0.2 ml).

TABLE 4

| Solution to be tested | Treated leg/untreated leg blood flow ratio (%) |
| --- | --- |
| Polymer[a] | 57.3 ± 4.5 |
| Compound 1 (0.1 mg)[a] | 60.5 ± 3.1 |
| Compound 1 MS (0.1 mg)[b] | 56.9 ± 5.6 |
| Compound 1 MS (0.1 mg)[a] | 68.4 ± 3.2* |

[a]Intramuscular administration into the ischemic left femoral part
[b]Intramuscular administration into right normal upper arm
**p < 0.01 vs. Polymer (Student's t-test)

Results:

Although significant increase in the blood flow was not found by the intramuscular administration of Compound 1 MS (0.1 mg) into the right normal upper arm, significant increase in the blood flow was found by the intramuscular administration of the same dose into the ischemic left femoral part. Based on this, it was suggested that efficacy of Compound 1 is not mediated by blood flow, but its topical administration into ischemic regions is important. In addition, since significant blood flow increasing action was not observed by the topical administration of Compound 1 into ischemic region, efficacy of the persistent preparation (MS) was suggested.

Example 7

Angiogenesis Test Using Rat Leg Ischemia (Arteriosclerosis Obliterans (ASO)) Model; Vasodilation Action and Angiogenesis Acceleration Action (In Vivo Test)

Leg ischemia model was prepared by ligating rat left femoral artery. Blood flow in hind legs was measured by using Laser Doppler Imager (Moor Instruments) 1 week after the preparation, and the animals were divided into 2 groups (n=5) in such a manner that the average value of blood flow became almost uniform.

Starting on the next day of the grouping, the solution to be tested was administered by intramuscular injection into the left femoral adductor (polymer group, Compound 1 MS group) for once a week, 4 times in total. Blood flows of hind legs were measured 3 days after the second administration (on the 10th day after grouping) and after 1 week and 2 weeks from the completion of the final administration, by using Laser Doppler Imager (Moor Instruments), and blood flows of the treated leg (left leg) and untreated leg (right leg) were compared and examined. The results of treated leg/untreated leg (%) are shown in Table 5.

In this connection, construction of the solution to be tested is as follows.
Polymer Group:
   The polylactic acid-glycolic acid copolymer used in Preparation Example 2 was suspended in 0.2 w/v % Tween 80 solution (0.2 ml). In this connection, amount of the polylactic acid-glycolic acid copolymer is identical to the amount contained in Compound 1 MS (0.3 mg).
Compound 1 MS (0.3 mg) Group:
   The microsphere preparation produced in Preparation Example 2 containing 0.3 mg of Compound 1 was suspended in 0.2 w/v % Tween 80 solution (0.2 ml).

TABLE 5

| | Treated leg/untreated leg blood flow ratio (%) | | | |
|---|---|---|---|---|
| Solution to be tested | Before 1st administration | After 3 days of 2nd administration | After 1 week of 4th administration | After 2 weeks of 4th administration |
| Polymer | 36.7 ± 4.2 | 49.8 ± 5.8 | 57.3 ± 4.5 | 61.3 ± 2.5 |
| Compound 1 MS (0.3 mg) | 36.6 ± 4.3 | 59.9 ± 3.7* | 72.7 ± 4.6* | 72.4 ± 5.7** |

*p < 0.05 vs. Polymer (Student's t-test)
**p < 0.01 vs. Polymer (Student's t-test)

Results:
   In comparison with the polymer-administered group, a significant blood flow increase of about 10% was observed at the ischemic region by Compound 1 MS (0.3 mg) even on the 10th day after the 1st administration (3 days after the 2nd administration). Since a period of about 4 weeks is necessary for angiogenesis and Compound 1 is under release at the ischemic topical region 3 days after the 2nd administration, it was suggested that this improving effect is a blood flow increasing effect by direct actions such as vasodilation action and platelet agglutination inhibitory action of slow-released Compound 1. In addition, a significant blood flow increase action of about 11% was also observed after 1 week and 2 weeks of the final administration. It was considered based on this that release of Compound 1 from the microsphere preparation was completely disappeared after one week of the final administration, and it was suggested that this effect is not the direct actions of Compound 1 (vasodilation action, platelet agglutination inhibitory action, etc.), but an effect by the angiogenesis action.

Example 8

Angiogenesis Test (In Vivo Test) Using Mouse Sponge Transplantation Model

Under anesthesia, dorsal part of a mouse was incised and a discus urethane sponge (about 5 mm in thickness and 13 mm in diameter) was embedded therein. Administration of the agent was carried out by topically administering it directly into the sponge once a day for a total of 14 times starting on the day of the sponge transplantation model preparation, or on the operation-completed day and 7th day thereafter. On the 15th day after the sponge transplantation, the sponge containing granulation tissue was extracted and observed with the naked eye, and then its wet mass was measured. In addition, this was mixed with distilled water of 4 times larger amount than the wet mass, homogenized and centrifuged, and then the supernatant was subjected to the measurement of the hemoglobin content using Hemoglobin 13-Test Wako (manufactured by Wako Pure Chemical Industries). Results of measurement of the total hemoglobin content in the extracted sponges are shown in Table 6.

In this connection, construction of the solution to be tested is as follows.
Polymer Group:
   The polylactic acid-glycolic acid copolymer used in Preparation Example 2 was suspended in 0.2 w/v % Tween 80 solution (0.05 ml). In this connection, amount of the polylactic acid-glycolic acid copolymer is identical to the amount contained in Compound 1 MS (200 µg).
Compound 1 (20 µg) Group:
   Compound 1 (20 µg) was suspended in 0.2 w/v % Tween 80 solution (0.05 ml).
Compound 1 (40 µg) Group:
   Compound 1 (40 µg) was suspended in 0.2 w/v % Tween 80 solution (0.05 ml).
Compound 1 (200 µg) Group:
   Compound 1 (200 µg) was suspended in 0.2 w/v % Tween 80 solution (0.05 ml).
Compound 1 MS (200 µg) group:
   The microsphere preparation produced in Preparation Example 2 containing 20014 of Compound 1 was suspended in 0.2 w/v % Tween 80 solution (0.05 ml).
Compound 1 MS (400 µg) Group:
   The microsphere preparation produced in Preparation Example 2 containing 400 µg of Compound 1 was suspended in 0.2 w/v % Tween 80 solution (0.05 ml).
Compound 3 (20 µg) Group:
   Compound 3 (20 µg) was suspended in 0.2 w/v % Tween 80 solution (0.05 ml).

TABLE 6

| Solution to be tested | Sponge wet weight (g) | Hemoglobin content (mg/g wet tissue) |
| --- | --- | --- |
| Polymer[b] | 0.4542 ± 0.0303 | 1.973 ± 0.564 |
| Compound 1 (20 μg)[a] | 0.3843 ± 0.0681 | 2.403 ± 0.533 |
| Compound 1 (40 μg)[a] | 0.5136 ± 0.0938 | 3.010 ± 0.808 |
| Compound 1 (200 μg)[b] | 0.4123 ± 0.0320 | 1.964 ± 0.289 |
| Compound 1 MS (200 μg)[b] | 0.5317 ± 0.1413 | 3.523 ± 0.482** |
| Compound 1 MS (400 μg)[b] | 0.5655 ± 0.1130 | 4.822 ± 1.218** |
| Compound 3 (20 μg)[a] | 0.5193 ± 0.0792 | 4.588 ± 0.488** |

[a] once a day, 14 days of repeated administration
[b] two administrations at 7 day intervals
**p < 0.01 vs. Polymer (Dunnett's test)

Results:

Formation of granulation was found in the sponges administered with Compound 1 MS (200 μg) (two administrations at 7 day intervals) and Compound 1 MS (400 μg) (two administrations at 7 day intervals), and they turned pale red, red or dark brown. In addition, when hemoglobin concentration in the granulation tissue formed in each sponge was measured, significant increase in the concentration of hemoglobin in comparison with the polymer group was observed so that the angiogenesis effect was confirmed. On the other hand, in the case of Compound 1 (20 μg) (14 days of repeated administration) and Compound 1 (40 μg) (14 days of repeated administration), hemoglobin concentration in the granulation tissue formed in each sponge showed an increasing tendency, but is not a significant increase. Also, hemoglobin concentration in the granulation tissue formed in the sponge did not increase in the case of Compound 1 (200 μg) (two administrations at 7 day intervals). Based on this, it was found that the slow release preparation of Compound 1 (Compound 1 MS) is particularly useful in inducing angiogenesis. Also, formation of granulation was found in the sponge administered with Compound 3 (20 μg) (14 days of repeated administration), and they turned pale red, red or dark brown. In addition, when hemoglobin concentration in the granulation tissue formed in the sponge was measured, significant increase in the concentration of hemoglobin in comparison with the polymer group was observed so that the angiogenesis effect was confirmed.

Example 9

Measurement of Angiogenesis Acceleration Action (In Vitro)

Test Method:

An angiogenesis kit (manufactured by Kurabo; constituted from normal human umbilical cord vein vascular endothelial cells and normal human skin fibroblasts) was cultured for 3 hours, and then the culture medium (the medium for angiogenesis use attached to the angiogenesis kit was used as the culture medium and cultured at 37° C. under a moist environment of 5% carbon dioxide-95% air, and a carbon dioxide incubator BNA-121D was used as the incubator) was changed and an agent to be tested was added to each well (0.5 ml/well). The medium exchange was carried out also on the 3rd, 6th and 8th days after commencement of the culturing and the fresh agent to be tested was added. The kind and concentration of the agent to be tested were untreated; DMSO: 0.1%; α-CD: 0.0118, 0.118 and 1.18 mg/ml; PGE2-αCD: 1, 10 and 100 nmol/l; Compound 3 (EP2 agonist), Compound 4 (EP4 agonist), EP1 agonist and EP3 agonist: 1, 10 and 100 nmol/l, VEGF: 0.1, 1 and 10 ng/ml; and HGF: 0.1, 1 and 10 ng/ml, and culturing was carried out by using 3 wells for each concentration. Fixation was carried out 10 days after the commencement of culturing, and staining of hollow organ with anti-CD31 antibody was carried out by using a hollow organ staining kit (manufactured by Kurabo). As the evaluation, Chalkley Grid (a grid lens, Kurabo) was mounted on the eyepiece of a microscope, and the hollow organ formation was evaluated by counting intersections of the randomly arrange points of Chalkley Grid with the formed hollow organ (by referring to the evaluation method of *J. Pathol.*, 177, 275-283 (1995)). The counting was carried out at 12 positions per well, and the total was calculated.

In this connection, Compound 3 as an EP2 agonist ((5Z, 9β,11α,13E)-17,17-propano-11,16-dihydroxy-9-chloro-20-norprost-5,13-dienoic acid) was dissolved in dimethyl sulfoxide (DMSO) to prepare $10^{-4}$, $10^{-5}$ and $10^{-6}$ mol/l solutions which were then used by diluting 1/1000 time with the culture medium.

Compound 4 as an EP4 agonist ((11α,13E,15α)-9-oxo-11, 15-dihydroxy-16-(3-methoxymethylphenyl)-17,18,19,20-tetranor-5-thiaprost-13-enoic acid) was dissolved in dimethyl sulfoxide (DMSO) to prepare $10^{-4}$, $10^{-5}$ and $10^{-6}$ mol/l solutions which were then used by diluting 1/1000 time with the culture medium.

The EP1 agonist ((13E)-(11α,15S,17S)-2,5-ethano-6,9-dioxo-11,15-dihydroxy-17,20-dimethylprost-13-enoic acid; the compound described in Example 1 in the specification of JP-A-11-322709) was dissolved in dimethyl sulfoxide (DMSO) to prepare $10^{-4}$, $10^{-5}$ and $10^{-6}$ mol/l solutions which were then used by diluting 1/1000 time with the culture medium.

The EP3 agonist (11α,15α-dimethoxy-9-oxoprost-5Z, 13E-dienoic acid; the compound described in Example 1 in the specification of WO98/34916) was dissolved in dimethyl sulfoxide (DMSO) to prepare $10^{-4}$, $10^{-5}$ and $10^{-6}$ mol/l solutions which were then used by diluting 1/1000 time with the culture medium.

The PGE2-αCD was dissolved in distilled water for injection to prepare $10^{-4}$, $10^{-5}$ and $10^{-6}$ mol/l solutions which were then used by diluting 1/1000 time with the culture medium.

As the VEGF (vascular endothelial growth factor), the 2 μg/ml solution of VEGF contained in the angiogenesis control reagent kit of Kurabo was diluted with the culture medium and used.

As the HGF (human hepatocyte growth factor), the 5 μg/ml solution of HGF purchased from R & D System-Funakoshi was diluted with the culture medium and used.

Statistical Analysis Method:

The counts of hollow organ formation in the untreated wells were compared with those of the wells treated with respective concentrations of test samples by Dunnett's test (two-sided test). The significance level was set to 5%.

In this connection, the data were shown by average value of 3 wells and standard deviation.

Figure 5:
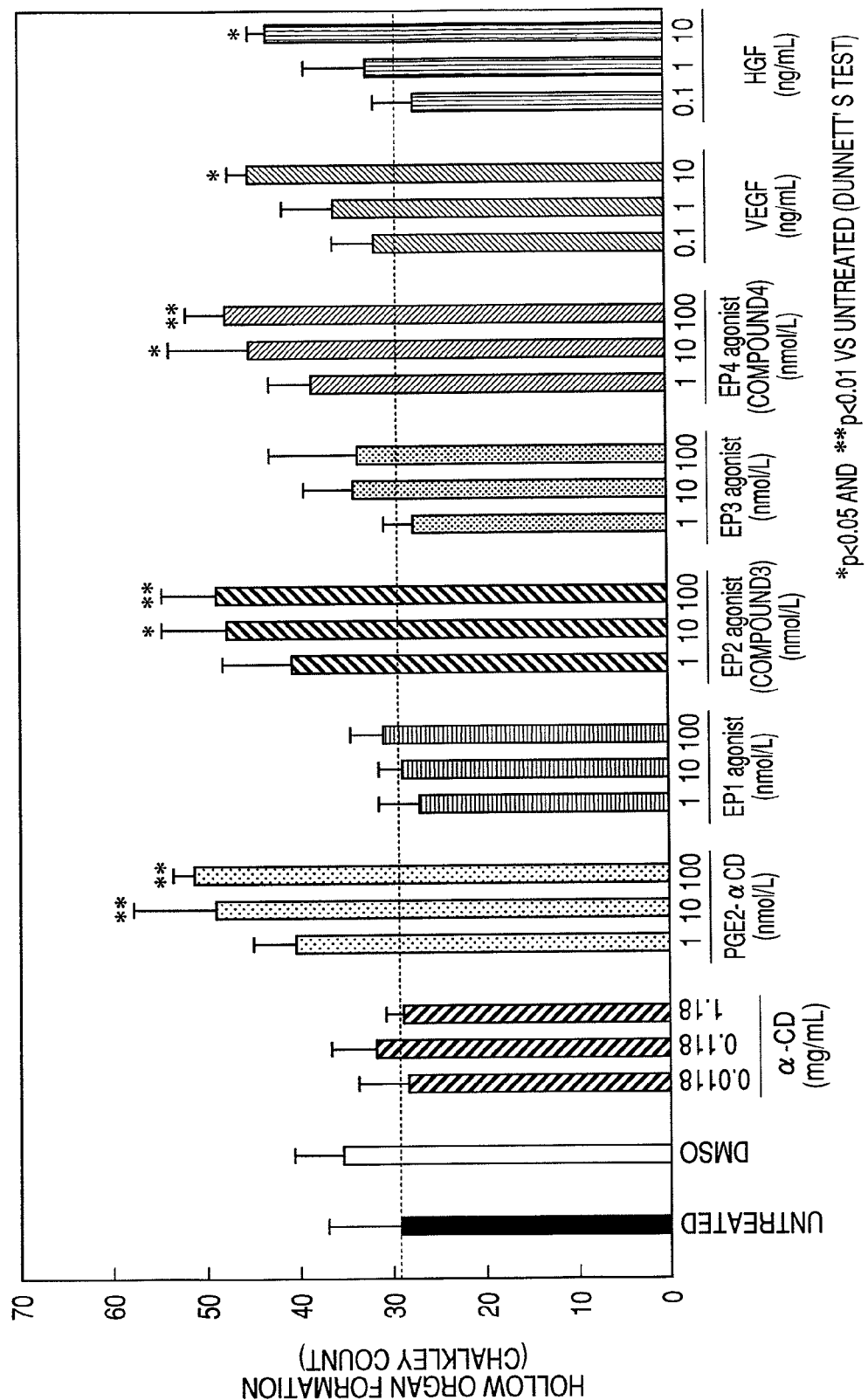
FIG. 5 shows a measured result of hollow organ formation acceleration actions of Compound 3 ((5Z,9β,11α,13E)-17,17-propano-11,16-dihydroxy-9-chloro-20-norprost-5,13-dienoic acid) and Compound 4 ((11α,13E,15α)-9-oxo-11,15-dihydroxy-16-(3-methoxymethylphenyl)-17,18,19,20-tetranor-5-thiaprost-13-enoic acid).

The test results are shown in FIG. 5.

Results:

The PGE2-αCD, Compound 3 (EP2 agonist) and Compound 4 (EP4 agonist) significantly accelerated hollow organ formation at concentrations of 10 nmol/l and 100 nmol/l. In addition, the VEGF and HGF accelerated hollow organ formation at a concentration of 10 ng/ml. However, the EP1 agonist, EP3 agonist and α-CD did not exert influence upon hollow organ formation.

Example 10

Measurement of Endogenous Repair Factor Releasing Action (In Vitro)

Test Method:

An angiogenesis kit (manufactured by Kurabo; constituted from normal human umbilical cord vein vascular endothelial cells and normal human skin fibroblasts) was cultured for 3 hours, and then the culture medium (the medium for angiogenesis use attached to the angiogenesis kit was used as the culture medium and cultured at 37° C. under a moist environment of 5% carbon dioxide-95% air, and a carbon dioxide incubator BNA-121D was used as the incubator) was changed and an agent to be tested was added to each well (0.5 ml/well). HGF and VEGF concentrations in the culture supernatants were measured 3 days after the commencement of the culturing. Kinds and concentrations of the agent to be tested were untreated; DMSO: 0.1%; PGE1-αCD: 100 nmol/l; PGE2-αCD: 100 nmol/l; and Compound 3 (EP2 agonist) and Compound 4 (EP4 agonist): 100 nmol/l, and the culturing was carried out by using 3 wells for each concentration. The HGF and VEGF concentrations were measured by using an ELISA kit (R % D system-Funakoshi).

In this connection, Compound 3 as an EP2 agonist ((5Z, 9β,11α,13E)-17,17-propano-11,16-dihydroxy-9-chloro-20-norprost-5,13-dienoic acid) was dissolved in dimethyl sulfoxide (DMSO) to prepare a $10^{-4}$ mol/l solution which was then used by diluting 1/1000 time with the culture medium.

Compound 4 as an EP4 agonist ((11α,13E,15α)-9-oxo-11, 15-dihydroxy-16-(3-methoxymethylphenyl)-17,18,19,20-tetranor-5-thiaprost-13-enoic acid) was dissolved in dimethyl sulfoxide (DMSO) to prepare a $10^{4}$ mol/l solution which was then used by diluting 1/1000 time with the culture medium.

The PGE1-αCD and PGE2-αCD were dissolved in distilled water for injection to prepare $10^{-4}$ mol/l solutions which were then used by diluting 1/1000 time with the culture medium.

Statistical Analysis Method:

HGF and VEGF concentrations in the supernatants of the solvent control group were compared with those of the agent-treated groups by Dunnett's test (two-sided test). The significance level was set to 5%.

In this connection, the data were shown by average value of 3 wells and standard deviation.

The test results after 72 hours of the culturing are shown in Table 7.

TABLE 7

| Agent tested | HGF (pg/ml) | VEGF (pg/ml) |
| --- | --- | --- |
| Untreated | 110 ± 16 | 2004 ± 76 |
| PGE1-αCD | 2043 ± 77*** | 2710 ± 50*** |
| PGE2-αCD | 1735 ± 95*** | 3032 ± 165*** |
| EP2 agonist (Compound 3) | 1865 ± 48*** | 2762 ± 51*** |
| EP4 agonist (Compound 4) | 379 ± 12*** | 2936 ± 69*** |

***$p < 0.001$ vs. untreated (Dunnett's test)

Results:

The PGE1-αCD, PGE2-αCD, Compound 3 (EP2 agonist) and Compound 4 (EP4 agonist) significantly increased HGF and VEGF concentrations in supernatants at a concentration of 100 nmol/l.

The invention claimed is:

1. A microsphere preparation comprising (E)-[5-[2-[1-phenyl-1-(3-pyridyl)methylideneaminoxy]ethyl]-7,8-dihydronaphthalen-1-yloxy]acetic acid or a salt thereof.

2. The microsphere preparation of claim 1, further comprising at least one biodegradable polymer.

3. The microsphere preparation of claim 2, wherein the at least one biodegradable polymer is
    selected from the group consisting of a polylactic acid, a polyglycolic acid, a lactic acid-glycolic acid copolymer and combinations thereof.

4. A method of treating myocardial infarction, angina pectoris, gastric ulcer, arteriosclerosis, congestive heart failure or coronary artery disease comprising:
    administering to a patient in need thereof a therapeutically effective amount of a microsphere preparation comprising (E)-[5-[2-[1-phenyl-1-(3-pyridyl)methylideneaminoxy]ethyl]-7,8-dihydro-naphthalen-1-yloxy]acetic acid or a salt thereof.

5. The method of claim 4, wherein the disease is myocardial infarction.

6. The method of claim 4, wherein the disease is congestive heart failure.

7. The method of claim 4, further comprising:
    accelerating production of a vascular endothelial growth factor (VEGF) and/or a hepatocyte growth factor (HGF).

8. The method of claim 5, further comprising:
    accelerating production of a vascular endothelial growth factor (VEGF) and/or a hepatocyte growth factor (HGF).

9. The method of claim 6, further comprising:
    accelerating production of a vascular endothelial growth factor (VEGF) and/or a hepatocyte growth factor (HGF).

10. A method of treating pulmonary hypertension, said method comprising:
    administering to a patient in need thereof a therapeutically effective amount of a microsphere preparation comprising (E)-[5-[2-[1-phenyl-1-(3-pyridyl)methylideneaminoxy]ethyl]-7,8-dihydro-naphthalen-1-yloxy]acetic acid or a salt thereof.

11. A method of treating chronic renal insufficiency, said method comprising:
    administering to a patient in need thereof a therapeutically effective amount of a microsphere preparation comprising (E)-[5-[2-[1-phenyl-1-(3-pyridyl)methylideneaminoxy]ethyl]-7,8-dihydro-naphthalen-1-yloxy]acetic acid or a salt thereof.

12. A method of treating dilated cardiomyopathy, said method comprising:
    administering to a patient in need thereof a therapeutically effective amount of a microsphere preparation comprising (E)-[5-[2-[1-phenyl-1-(3-pyridyl)methylideneaminoxy]ethyl]-7,8-dihydro-naphthalen-1-yloxy]acetic acid or a salt thereof.

13. The method of claim 10, further comprising:
    accelerating production of vascular endothelial growth factor (VEGF) and/or hepatocyte growth factor (HGF).

14. The method of claim 11, further comprising:
    accelerating production of vascular endothelial growth factor (VEGF) and/or hepatocyte growth factor (HGF).

15. The method of claim 12, further comprising:
    accelerating production of vascular endothelial growth factor (VEGF) and/or hepatocyte growth factor (HGF).

16. The microsphere preparation of claim 1, 2 or 3, further comprising:
    (i) a low molecular compound, (ii) a high molecular protein, (iii) a polypeptide, (iv) a polynucleotide, (v) an antisense molecule, (vi) a decoy molecule, (vii) an antibody, (viii) a vaccine, (ix) a stem cell, or (x) a combination of more than one of (i) to (ix).

* * * * *